(12) United States Patent
Herr et al.

(10) Patent No.: US 9,682,005 B2
(45) Date of Patent: Jun. 20, 2017

(54) ELASTIC ELEMENT EXOSKELETON AND METHOD OF USING SAME

(71) Applicant: Massachusetts Institute of Technology, Cambridge, MA (US)

(72) Inventors: Hugh M. Herr, Somerville, MA (US); Grant Elliott, Cambridge, MA (US); Andrew Marecki, Somerville, MA (US); Hazel Briner, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 899 days.

(21) Appl. No.: 13/774,774

(22) Filed: Feb. 22, 2013

(65) Prior Publication Data
US 2013/0296746 A1 Nov. 7, 2013

Related U.S. Application Data

(60) Provisional application No. 61/602,851, filed on Feb. 24, 2012.

(51) Int. Cl.
*G06F 19/00* (2011.01)
*A61H 3/00* (2006.01)
(Continued)

(52) U.S. Cl.
CPC ............... *A61H 3/00* (2013.01); *B25J 9/104* (2013.01); *A61F 2002/2825* (2013.01); *A61F 2002/5018* (2013.01); *A61F 2002/7887* (2013.01)

(58) Field of Classification Search
CPC ............ A61H 3/00; A61F 2002/2825; A61F 2002/5018; A61F 2002/6845; A61F 2002/7887
(Continued)

(56) References Cited

U.S. PATENT DOCUMENTS 420,179 A  1/1890 Yagn
438,830 A  10/1890 Yagn
(Continued)

FOREIGN PATENT DOCUMENTS

DE  10219662 A1  11/2003
GB  2260083 A  4/1993
(Continued)

OTHER PUBLICATIONS

Office Action in regards to U.S. Appl. No. 13/722,246, entitled "A Robotic System for Simulating a Wearable Device and Method of Use," Date of Mailing: Dec. 4, 2015.
(Continued)

*Primary Examiner* — McDieunel Marc
(74) *Attorney, Agent, or Firm* — Hamilton, Brook, Smith & Reynolds, P.C.

(57) ABSTRACT

Running in a mammal, such as a human, is augmented by adaptively modulating anticipation of maximum leg extension of a mammal when running, and actuating an exoskeletal clutch linked in series to at least one elastic element, wherein the clutch and elastic element form an exoskeleton and are attached in parallel to at least one muscle-tendon unit of a leg of the mammal and span at least one joint of the mammal fitted with the exoskeleton. The exoskeletal clutch is actuated in advance of a predicted maximum extension of the exoskeletal clutch to thereby cause the exoskeletal clutch to lock essentially simultaneously with ground strike by the leg of the mammal. The elastic element is thereby engaged during stance phase of the gait of the mammal while running, and subsequently is disengaged prior to or during the swing phase of the gait of the mammal, thereby augmenting running of the mammal.

27 Claims, 24 Drawing Sheets

(51) Int. Cl.
    *B25J 9/10* (2006.01)
    *A61F 2/28* (2006.01)
    *A61F 2/50* (2006.01)
    *A61F 2/78* (2006.01)

(58) Field of Classification Search
    USPC .................. 700/245; 623/32, 35, 623; 703/3
    See application file for complete search history.

(56) References Cited

U.S. PATENT DOCUMENTS

| | | | |
|---|---|---|---|
| 440,684 A | 11/1890 | Yagn | |
| 3,449,769 A | 6/1969 | Mizen | |
| 4,986,280 A * | 1/1991 | Marcus | A61B 5/103 33/512 |
| 5,016,869 A | 5/1991 | Dick et al. | |
| 6,719,671 B1 | 4/2004 | Böck | |
| 6,741,911 B2 * | 5/2004 | Simmons | B25J 9/0006 318/568.11 |
| 7,313,463 B2 | 12/2007 | Herr et al. | |
| 8,244,402 B2 * | 8/2012 | Wells | G06K 9/3216 318/568.11 |
| 8,483,816 B1 | 7/2013 | Payton et al. | |
| 8,500,823 B2 | 8/2013 | Herr et al. | |
| 8,512,415 B2 | 8/2013 | Herr et al. | |
| 8,801,641 B2 | 8/2014 | Kazerooni et al. | |
| 8,945,028 B2 | 2/2015 | Kazerooni et al. | |
| 9,060,884 B2 | 6/2015 | Langlois | |
| 9,498,401 B2 | 11/2016 | Herr et al. | |
| 2004/0127825 A1 | 7/2004 | Castillo et al. | |
| 2006/0004307 A1 * | 1/2006 | Horst | A61H 1/0237 601/5 |
| 2006/0150753 A1 | 7/2006 | Massimo et al. | |
| 2006/0211956 A1 | 9/2006 | Sankai | |
| 2008/0009771 A1 | 1/2008 | Perry et al. | |
| 2009/0055019 A1 | 2/2009 | Stiehl et al. | |
| 2010/0241242 A1 | 9/2010 | Herr et al. | |
| 2010/0324699 A1 | 12/2010 | Herr et al. | |
| 2011/0040216 A1 | 2/2011 | Herr et al. | |
| 2011/0264230 A1 | 10/2011 | Herr et al. | |
| 2012/0179075 A1 | 7/2012 | Perry et al. | |
| 2013/0150761 A1 | 6/2013 | Romo et al. | |
| 2013/0158444 A1 | 6/2013 | Herr et al. | |
| 2013/0197318 A1 | 8/2013 | Herr et al. | |
| 2013/0282141 A1 | 10/2013 | Herr et al. | |
| 2013/0289452 A1 * | 10/2013 | Smith | B25J 9/0006 601/33 |
| 2013/0310979 A1 | 11/2013 | Herr et al. | |
| 2015/0173929 A1 * | 6/2015 | Kazerooni | A61F 5/0125 602/16 |
| 2015/0209214 A1 | 7/2015 | Herr et al. | |

FOREIGN PATENT DOCUMENTS

| | | |
|---|---|---|
| WO | WO 2009/149206 A2 | 12/2009 |
| WO | WO 2010/088635 A1 | 8/2010 |
| WO | WO 2012/175211 A1 | 12/2012 |
| WO | WO 2013/142343 A1 | 9/2013 |
| WO | WO 2014/151065 A2 | 9/2014 |
| WO | WO 2015/095211 A2 | 6/2015 |

OTHER PUBLICATIONS

Abul-Haj, C., & Hogan, N. "An emulator system for developing improved elbow-prosthesis designs," IEEE Transactions on Biomedical Engineering, 9:724-737 (1987).
Andersen, J. B., & Sinkjaer, T. "Mobile ankle and knee perturbator," IEEE Transactions on Biomedical Engineering, 50(10): 1208-1211 (2003).
Andersen, J. B.,& Sinkjaer, T. "An actuator system for investigating electrophysiological and biomechanical features around the human ankle joint during gait", IEEE Transactions on Rehabilitation Engineering, 3(4): 299-306 (1995).
Caputo, J. M. and Collins, S. H. (Aug. 2012) "Externally powered and controlled ankle-foot prosthesis," Annual meeting of American Society of Biomechanics, 2012—Poster.
Caputo, J. M. and Collins, S. H. (Aug. 2012) "Externally powered and controlled ankle-foot prosthesis," Annual meeting of American Society of Biomechanics, 2012.—Abstract.
Caputo, J. M., and Collins, S. H. (Jul. 2011) "Externally powered and controlled ankle-foot prosthesis," In Dynamic Walking, 2011 International Conference—Abstract.
Caputo, J. M., and Collins, S. H. (Jul. 2011) "Ankle-foot prosthesis testbed." In Dynamic Walking, 2011 International Conference—Poster.
Collins, S. H. (Jul. 2011) "Developing ankle control strategies with an experimental biomechatronic testbed," In Dynamic Walking, 2011 International Conference on.—Slides.
Collins, S. H. (Jul. 2011) "Exploring ankle control strategies with an experimental biomechatronic testbed," in Dynamic Walking, 2011 International Conference on.—Abstract.
Flowers, W. C. (1973). "A man-interactive simulator system for above-knee prosthetics studies," Dissertation, Massachusetts Institute of Technology.
Jackson, R. W. and Collins S. H. (May 2012) "Targeting specific muscles for rehabilitation with an EMG-controlled ankle-foot orthosis," In Dynamic Walking, 2012 International Conference—Slides.
Jackson, R. W. and Collins S. H. (May 2012) "Targeting specific muscles for rehabilitation with an EMG-controlled ankle-foot orthosis," In Dynamic Walking, 2012 International Conference—Abstract.
Sawicki, G. S., Gordon, K. E., & Ferris, D. P. (Jul. 2005). "Powered lower limb orthoses: applications in motor adaptation and rehabilitation," IEEE in Rehabilitation Robotics, 2005, ICORR 2005, 9$^{th}$ International Conference (pp. 206-211).
Schiele, A. "Fundamentals of Ergonomic Exoskeleton Robots." Doctoral dissertation, Ph.D. Thesis, Delft University of Technology, 2008, available at: www.library.tudelft.nl.
Sulzer, J. S., Holz, R. A., Peshkin,M, A., & Patton, J. L. "A highly backdrivable, lightweight knee actuator for investigating gait in stroke," IEEE Transactions on Robotics,, 25(3): 539-548 (2009).
Veneman, J. F. (2007). "Design and evaluation of the gait rehabilitation robot LOPES." University of Twente. Ph.D. Dissertation.
Alexander, R. M., "Energy-saving mechanisms in walking and running," *Journal of Experimental Biology*, 160:55-69 (1991).
Au, S., "Powered ankle-foot prosthesis for the improvement of amputee walking economy," Doctoral dissertation, Massachusetts Institute of Technology (2007).
Belli, A., et al., "Moment and power of lower limb joints in running," *International Journal of Sports Medicine*, 23:136-141 (2002).
Biewener, A. A., "Muscle function in vivo: A comparison of muscles used for elastic energy savings versus muscles used to generate mechanical power," *American Zoology*, 38:703-717 (1998).
Blaya, J. A., and Herr, H., "Adaptive control of a variable-impedance ankle-foot orthosis to assist drop-foot gait," IEEE Transactions on Neural Systems & Rehabilitation Engineering.12(1):24-31 (2004).
Brockway, J. M., et al., "Derivation of formulae used to calculate energy expenditure in man," *Human Nutrition Clinical Nutrition*, 41:463-471 (1987).
Cavagna, G. A., "Force platforms as ergometers," *Journal of Applied Physiology*, 39(1):174-179 (1985).
Cavagna, G. A., et al., "Mechanical work in terrestrial locomotion: Two basic mechanisms for minimizing energy expenditure," *American Journal of Physiology Regulatory, Integrative, and Comparative Physiology*, 233:243-261 (1977).
Clancy, E. A., et al., "Sampling, noise-reduction, and amplitude estimation issues in surface electromyography," *Journal of Electromyography and Kinesiology*, 12:1-6 (2002).
Collins, J. A., "*Mechanical Design of Machine Elements and Machines*," John Wiley and Sons, Hoboken, N.J., Table of Contents (2003).

(56) References Cited

OTHER PUBLICATIONS

Cram, J. R., et al., "*Introduction to Surface Electromyography,*" Aspen Publishers, Inc., Table of Contents (1998).
Cyberdyne, (2010). What's HAL (Hybrid Assistive Limb®) Available: http://www.cyberdyne.jp/english/robotsuithal/ downloaded Jan. 15, 2014.
Dollar, A. M. and Herr, H., "Lower extremity exoskeletons and active Orthoses," Challenges and state-of-the-art, *IEEE Transactions on Robotics*, 24(1):144-158 (2008).
Dollar, A. M. and Herr, H., "Design of a quasi-passive knee exoskeleton to assist running," *Proceedings of the 2008 IEEE/RSJ International Conference on Intelligent Robots and Systems*, Nice, France, Sep. 2008.
Dollar, A. M. and Herr, H., "Active orthoses for the lower-limbs—Challenges and state of the art," *Proceedings of the 2007 IEEE International Conference on Rehabilitation Robotics (ICORR)*, Noordwijk, Netherlands, pp. 968-977, Jun. 2007.
Elliott, G. A., "Design and Evaluation of a Quasi-Passive Robotic Knee Brace: On the Effects of Parallel Elasticity on Human Running." Doctoral dissertation, Massachusetts Institute of Technology (2012).
Farley, C. T. and Ferris, D.P., "Biomechanics of walking and running. From center of mass movement to muscle action," *Exercise and Sport Sciences Reviews*, 26(1):253-285 (1998).
Farley, C. T. and Gonzalez, O., "Leg stiffness and stride frequency in human running," *Journal of Biomechanics*, 29(2):181-186 (1996).
Farris, D. J. and Sawicky, G.S., "The mechanics and energetics of human walking and running—A joint level perspective," *Journal of the Royal Society Interface*, 9(66):110-118 (2012).
Ferris, D. P., "Running in the real world: Adjusting leg stiffness for different surfaces," *Proceedings Biological Sciences*, 265:989-994 (1998).
Ferris, D. P., et al., "Neuromechanical adaptation to hopping with an elastic ankle-foot orthosis," *Journal of Applied Physiology*, 100:163-170 (2006).
Ferris, D. P., et al., "Runners adjust leg stiffness for their first step on a new running surface," *Journal of Biomechanics*, 32:787-794 (1999).
Grabowski, A. M. and Herr, H.M., "Leg exoskeleton reduces the metabolic cost of human hopping," *Journal of Applied Physiology*, 107:670-678 (2009).
He, J., et al., "Mechanics of running under simulated low gravity," *Journal of Applied Physiology*, 71:863-870 (1991).
Herr, H., "Exoskeletons and orthoses: classification, design challenges and future directions," *Journal of Neuro Engineering and Rehabilitation*, 6(1): (2009).
Herr, H. M. et al. "Patient-adaptive prosthetic and orthotic leg systems," Proceedings of the 12th Nordic Baltic Conference on Biomedical Engineering and Medical Physics, Reykjavik, Iceland, pp. 123-128, Jun. 2002.
Herr, H. and Langman, N., "Optimization of human-powered elastic mechanisms for endurance amplification," Structural Optimization, vol. 13, No. 1, pp. 65-67, Feb. 1997.
HULC-Lockheed Martin, www.lockheedmartin.com/us/products/hulc.html. Downloaded Jan. 15, 2014.
Kawamoto, H. and Sankai, Y., "Power assist method based on phase sequence and muscle force condition for HAL," *Advanced Robotics*, 19 (7):717-734 (2005).
Kazerooni, H. and Kim, S., "Contact instability of the direct drive robot when constrained by a rigid environment," In *ASME Winter Annual Meeting*, (1989).
Kazerooni, H., et al., "On the control of the Berkeley lower extremity exoskeleton (BLEEX)," In *IEEE International Conference on Robotics and Automation*, Apr. 2005.
Kerdok, A. E., et al., "Energetics and mechanics of human running on surfaces of different stiffnesses," *Journal of Applied Physiology*, 92:469-478 (2002).
Lee, C. R. and Farley, C.T., "Determinants of the center of mass trajectory in human walking and running," *Journal of Experimental Biology*, 201:2935-2944 (1998).
Martinez-Villalpando, E. C., et al., "Design of an agonist-antagonist active knee prosthesis," IEEE conference, *Biomedical Robotics and Biomechatronics*, Scottsdale, AZ Oct. 2008.
Martínez-Villalpando, E. C., "Design and Evaluation of a Biomimetic Agonist-Antagonist Active Knee Prosthesis." Doctoral dissertation, Massachusetts Institute of Technology (2012).
McMahon, T. A. and Cheng, G. C., "The mechanics of running: How does stiffness couple with speed?" *Journal of Biomechanics*, 23(1):65-78 (1990).
McMahon, T. A., "*Muscles, Reflexes, and Locomotion,*" Princeton University Press, Princeton, N.J., Table of Contents (1984).
Merletti, R., Standards for reporting EMG data, Technical report, Politecnico di Torino (1999).
Mosher, R. S., "Handyman to Hardiman," Technical report, General Electric Research and Development Center (1967).
Munro, C. F., et al., "Ground reaction forces in running: a reexamination," *Journal of Biomechanics*, 20(2):147- 155 (1987).
Novacheck, T. F., The biomechanics of running. *Gait and Posture*, 7:77-95 (1998).
Pratt, G. A. and Williamson, M. M., "Series elastic actuators," In *IEEE International Conference on Intelligent Robots and Systems*, 1:399-406 (1995).
Sawicki, G. S. and Ferris, D. P., "Mechanics and energetics of incline walking with robotic ankle exoskeletons," *The Journal of Experimental Biology*, 212:32-41 (2008).
Stock Drive Products, *Elements of Metric Gear Technology*, New Hyde Park, NY, at least as early as Jan. 15, 2014.
Valiente, A., "Design of a quasi-passive parallel leg exoskeleton to augment load carrying for walking," Master's thesis, Massachusetts Institute of Technology (2005).
Walsh, C. J., "Biomimetic design of an under-actuated leg exoskeleton for load-carrying augmentation," Master's thesis, Massachusetts Institute of Technology (2006).
Walsh, C. et al., "A quasi-passive leg exoskeleton for load-carrying augmentation," *International Journal of Humanoid Robotics*, 4(3):487-506 (2007).
Walsh, C. J. et al., "An autonomous, underactuated exoskeleton for load-carrying augmentation," *IEEE/RSJ International Conference on Intelligent Robots and Systems (IROS)*, Beijing, China, Oct. 2006.
Walsh C. J., et al., "Development of a lightweight, underactuated exoskeleton for load-carrying augmentation," *Proceedings of the IEEE International Conference on Robotics and Automation*, Orlando, FL, May 2006.
Wiggin, M. B., et al., "An exoskeleton using controlled energy storage and release to aid ankle propulsion," In *2011 IEEE International Conference on Rehabilitation Robotics Rehab Week*, Zurich, Switzerland Jun. 29-Jul. 1, 2011.
Zoss, A., et al., On the mechanical design of the Berkeley lower extremity exoskeleton (BLEEX), In *IEEE International Conference on Intelligent Robots and Systems* (2005).
Elliott, G., et al., "The Biomechanics and Energetics of Human Running using an Elastic Knee Exoskeleton," *International Conference on Rehabilitation Robotics* (2013).
Au, S.K., et al., "Biomechanical Design of a Powered Ankle-Foot Prosthesis," Proceedings IEEE $10^{th}$ International Conference on Rehabilitation Robotics, Noordwijk, The Netherlands, Jun. 2007.
Au, S.K., et al., "Powered Ankle-Foot Prosthesis for the Improvement of Amputee Ambulation," $29^{th}$ IEEE Conference, Lyon, France, Aug. 2007.
Asbeck, A. T., et al., "Biologically-inspired Soft Exosuit", 2013 IEEE Int'l Conf. on Rehabilitation Robotics (Jun. 24-26, 2013).
Bogue, R., "Exoskeletons and Robotic Prosthetics: A Review of Recent Developments," *Industrial Robot: An International Journal*, 36(5): 421-427 (2009).
Cherry, M. S. et al., "An Elastic Exoskeleton for Assisting Human Running," in *Proceedings of the ASME 2009 International Design Engineering Technical Conferences & Computers and Information in Engineering Conference*, pp. 1-12 (2009).

(56) References Cited

OTHER PUBLICATIONS

Herr, H., "The new bionics that let us run, climb and dance", TED 2014; Filmed Mar. 2014; Available at: https://www.ted.com/talks/hugh_her_the_new_bionics_that_let_us_run_climb_and_dance (Retrieved from the Internet on Apr. 15, 2015).

International Search Report and Written Opinion of the International Searching Authority, PCT/US2014/070636, date of mailing Aug. 25, 2015, "Optimal Design of a Lower Limb Exoskeleton or Orthosis".

Karlin, S., "Raiding Iron Man's Closet," *IEEE Spectrum*, .48(8), p. 25 (Aug. 2011).

Kuan, J. et al., "Design of a Knee Joint Mechanism that Adapts to Individual Physiology", *Engineering in Medicine and Biology Society (EMBS)*, 2014, 36th Annual Conference of the IEEE, pp. 2061-2064 (Aug. 26-30, 2014).

Kuan, J. et al., "Tethered Wearable Robot System for Augmentation and Rehabilitation," *Biomechatronics Group, Media Lab, Massachusetts Institute of Technology*, (Nov. 6, 2012).

Lockheed Martin, Product Finder, Press Releases, "HULC", Available at: http://www.lockheedmartin.com/products/hulc/ (Retrieved from the Internet on Jan. 15, 2014).

Non-Final Office Action mailed Mar. 7, 2016 for U.S. Appl. No. 13/774,774.

Non-Final Office Action mailed on Dec. 4, 2015 for U.S. Appl. No. 13/722,246, entitled "A Robotic System for Simulating a Wearable Device and Method of Use."

PRNewswire, Raytheon Unveils Lighter, Faster, Stronger Second Generation Exoskeleton Robotic Suit (Sep. 27, 2010; Available at: http://multivu.prnewswire.com/mnr/raytheon/46273 (Retrieved from the Internet on Jan. 21, 2014).

Wehner, M., et al., "A Lightweight Soft Exosuit for Gait Assistance", 2013 IEEE Int'l Conf. on Robotics and Automation (ICRA) (May 6-10, 2013).

Zelinsky, A., "Robot Suit Hybrid Assistive Limb," *IEEE Robotics & Automation Magazine*, 16(4): pp. 98 and 102 (2009).

\* cited by examiner

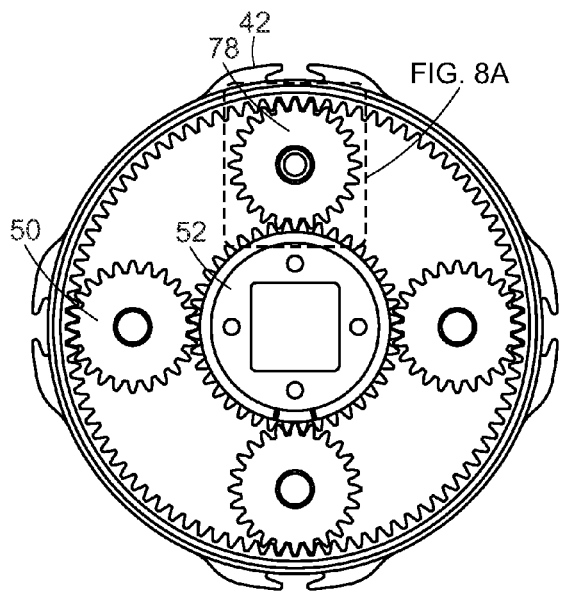
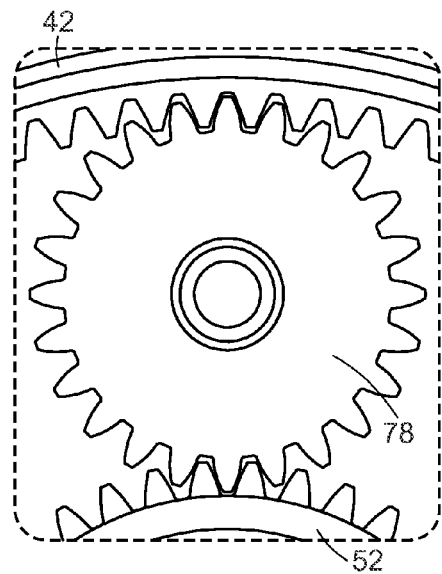
FIG. 8　　　　FIG. 8A
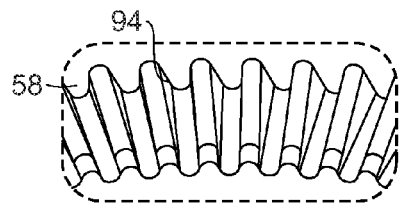
FIG. 9A
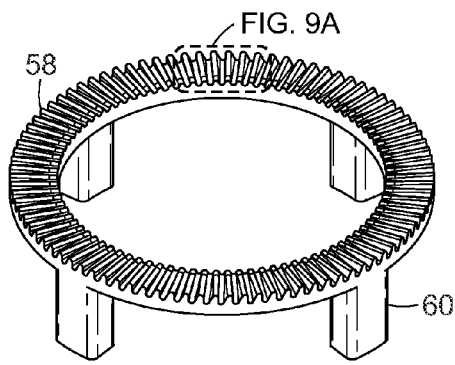
FIG. 9

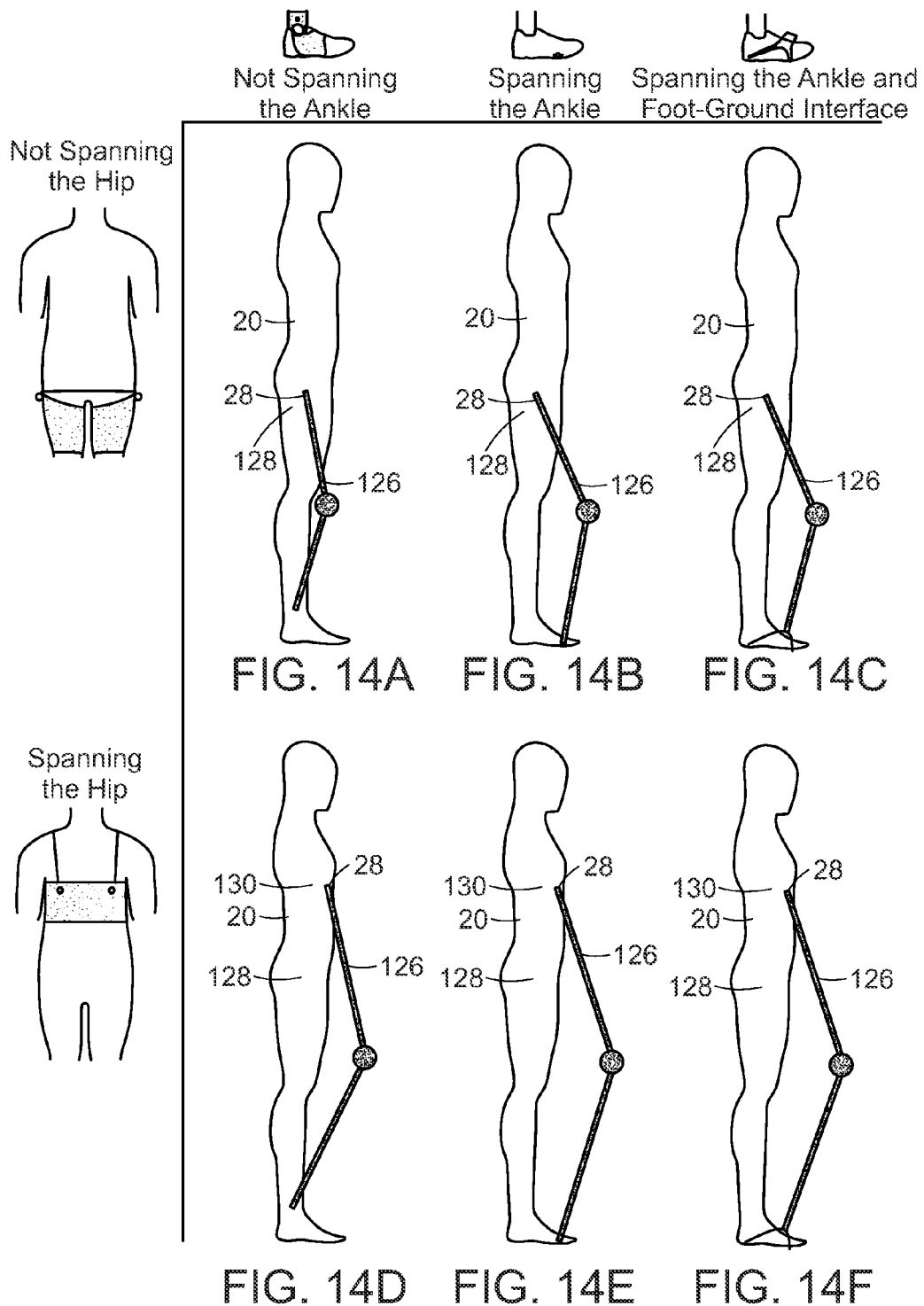

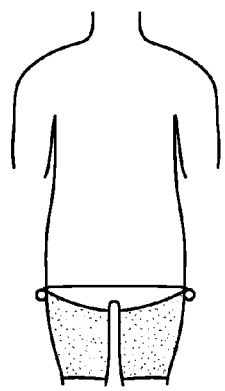 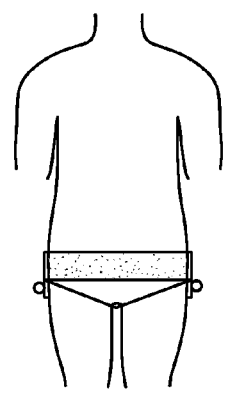
FIG. 15A    FIG. 15B
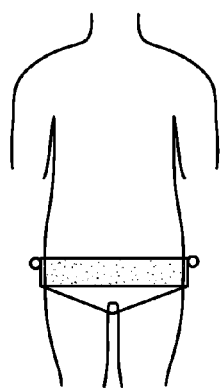 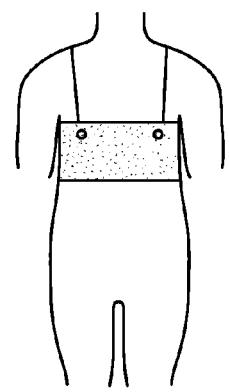
FIG. 15C    FIG. 15D
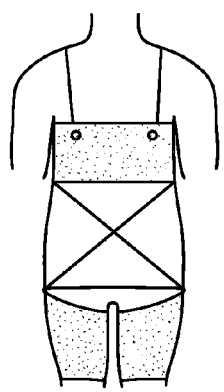
FIG. 15E

ELASTIC ELEMENT EXOSKELETON AND METHOD OF USING SAME

RELATED APPLICATION(S)

This application claims the benefit of U.S. Provisional Application No. 61/602,851, filed on Feb. 24, 2012.

The entire teachings of the above application are incorporated herein by reference.

BACKGROUND OF THE INVENTION

Metabolic augmentation of human locomotion has proved an elusive goal. Although a number of exoskeletons have been built, none has demonstrated a significant reduction in metabolic demand of locomotion. Exoskeletons may loosely be classified as intended to augment human capabilities, such as load capacity or ambulatory speed, or to increase human endurance, by lowering the metabolic demand of the given activity. For example, an exoskeletal device intended to reduce the metabolic demand of movement may alternatively permit the execution of that movement at higher speed for a given metabolic demand. Other devices, intended to restore lost functionality, may also be thought of as exoskeletons.

Exoskeletons are classified as passive, quasi-passive or active, based on the usage of power. Passive exoskeletons require no energy source and generally consist of linkages, springs, and dampers. They typically rely on mechanisms, are less robust and, consequently, may result in behavior that may lead or lag what is intended. Active devices, in contrast, add energy to the gait cycle, usually through motors or hydraulic cylinders. Active systems are often limited by weight limitations necessary to minimize changes in momentum that occur during gait cycles, particularly during running. Quasi-passive devices lie between passive and active devices, being unable to inject energy into the gait cycle, but nonetheless requiring a power supply, usually to operate electronic control systems, clutches or variable dampers. Typically, although not necessarily, the power requirements of a quasi-passive device are relatively low. Further, exoskeletons, whether active, passive or quasi-passive, may be described as primarily acting in series or in parallel with a subject's limbs.

Moreover, the mechanics of walking and running are significantly different. Specifically, walking resembles, and can be modeled as, an inverted pendulum wherein kinetic and gravitational potential energies are substantially out of phase. During running, however, kinetic and gravitational potential energies are almost perfectly in phase, whereby the center of mass and, thus, potential energy are highest at essentially the same time as each other. In other words, during running, elastic potential energy is stored in muscle-tendon units in a cycle that is out of phase with kinetic and gravitational potential energy. Generally, active, passive and quasi-passive exoskeletons do not accommodate the running gait of a legged animal, such as a mammal, including, for example, a human wherein the center of mass and, thus, potential energy is highest at approximately the same time velocity and, thus, kinetic energy is highest (in phase), and, whereby elastic potential energy must be stored out of phase with kinetic and gravitational potential energy.

Therefore, a need exists for an exoskeleton that can augment running in a mammal, such as a human, that overcomes or minimizes the above-referenced difficulties.

SUMMARY OF THE INVENTION

The present invention is directed to a method for augmenting running in a mammal, such as a human, and to a clutched elastic element exoskeleton that employs the method of the invention.

In one embodiment, the method for augmenting running in a mammal includes the steps of adaptively modulating anticipation of a maximum extension of an exoskeletal clutch attached to the leg of a mammal when running. The exoskeletal clutch is linked to at least one elastic element to form an exoskeleton, wherein the clutch and the elastic element are attached in parallel to at least one muscle-tendon unit of the leg of the mammal. The exoskeletal clutch is actuated in advance of a predicted maximum extension of the exoskeletal clutch, to thereby cause the exoskeletal clutch to lock essentially simultaneously with the ground strike by the mammal, whereby the elastic element is engaged during a stance phase of the gate of the mammal while running. The elastic element is disengaged prior to or during a swing phase of the gait of the mammal, thereby augmenting running of the mammal.

In one particular embodiment of the method of the invention, adaptively modulating maximum extension of the exoskeletal clutch includes correlating a position of the exoskeletal clutch and an angular velocity of the exoskeleton in a sagittal plane of the mammal with a phase of the gait cycle of the mammal while running, to thereby estimate the predicted maximum extension of the exoskeletal clutch prior to ground strike of the leg of the mammal while running.

In a further embodiment of the invention, adaptively modulating anticipation of maximum extension of the exoskeletal clutch further includes, upon or after estimating the predicted maximum extension, correlating past positions of the exoskeletal clutch during a terminal swing phase with each other to thereby predict maximum extension of the exoskeletal clutch while running.

One clutched elastic element exoskeleton of the invention includes a longitudinal harness, including a proximal component and a distal component. A rotary clutch assembly is linked in series to at least one elastic element, wherein the rotary clutch assembly and the elastic element span the proximal and distal components, and wherein a major longitudinal axis of each elastic element extends through and is rotatable about a center of rotation at the rotary clutch.

The invention has many advantages. For example, by adaptively modulating anticipation of maximum extension of an exoskeletal clutch attached to the leg of the mammal when running, the clutch employed by the method can be locked essentially simultaneously with ground strike of the leg, thereby maximizing storage of potential energy upon and after ground strike. Further, as a quasi-passive device, use of heavy motors and external energy storage is avoided, thereby minimizing energy loss by changes in momentum associated with leg movement while running. Further, the method and apparatus of the invention accommodate changes in stride associated with changes: i) from running to walking and the reverse; ii) in velocity; and iii) to changes in terrain, including stairs and ramps. Further, the advantages of the invention are not limited by any particular stride. For example, when the mammal is a human, the method and device of the invention are not impaired by whether the human subject runs by striking the ground first with the heel or ball of the foot.

BRIEF DESCRIPTION OF THE DRAWINGS

FIGS. 8 and 8A are plan and detail views of the interior of the rotary clutch of FIG. 4 showing the ring gear, planet gears and sun gear.

FIGS. 9 and 9A are perspective and detail views of a translating clutch plate of the rotary clutch of the invention.

FIGS. 14A through 14F are schematic representations of various exemplary embodiments of exoskeletons of the invention employing a rotary clutch.

FIGS. 15A through 15E are schematic representations of various exemplary embodiments of harnesses employed to mount proximal portions of exoskeletons of the invention to a subject.

DETAILED DESCRIPTION OF THE INVENTION

The invention generally is directed to a method for augmenting running in a mammal, such as a human, and to a clutched elastic element exoskeleton that can employ the method of the invention.

The method for augmenting running in a mammal and the clutched elastic exoskeleton of the invention can apply relatively high torque with high resolution to a joint of the mammal during running while employing relatively low mass, thereby overcoming the problems associated with the relatively high mass of active devices and the delayed reaction time of passive devices. Further, the method and apparatus of the invention do not depend upon any particular configuration of attachment to the mammal subject, and accommodate changes in stride and transitions between walking and running, inclines and declines of surfaces, and ascent and descent of stairs.

Figure 1:
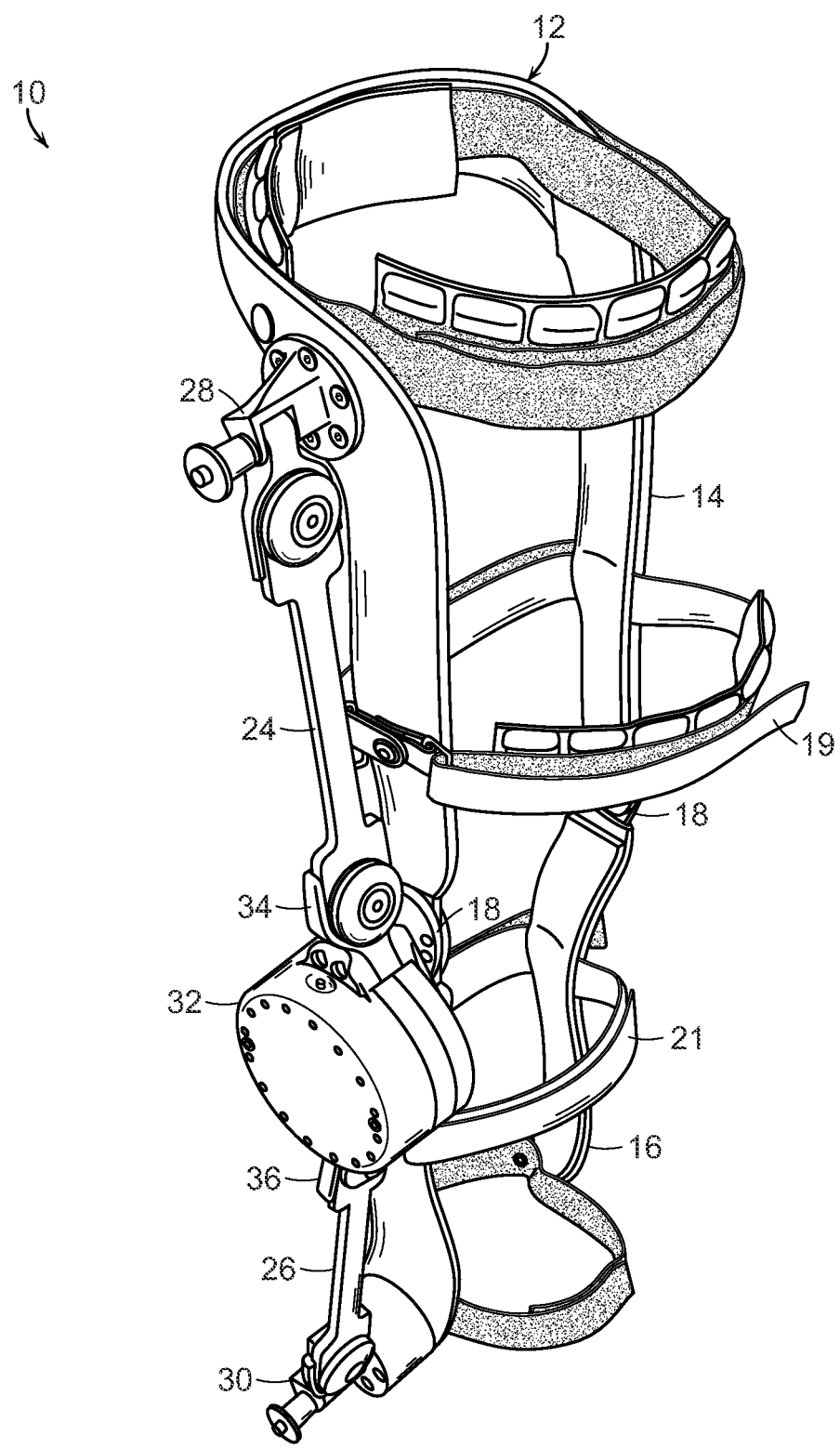
FIG. 1 is a perspective view of one embodiment of the exoskeleton of the invention.
Figure 2:
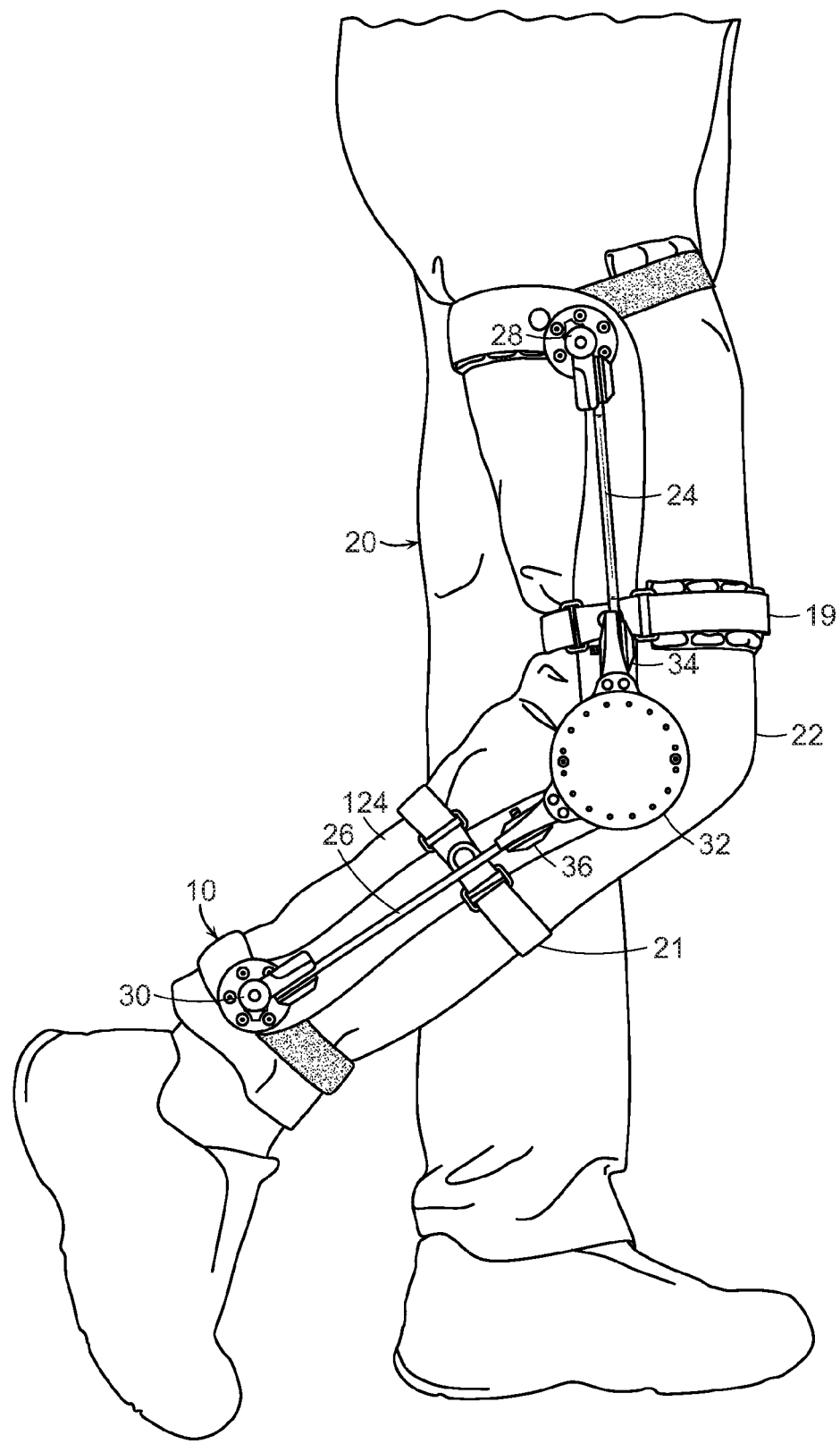
FIG. 2 is a side view of the exoskeleton shown in FIG. 1 while being worn by a subject at toe-off while walking.
Figure 3:
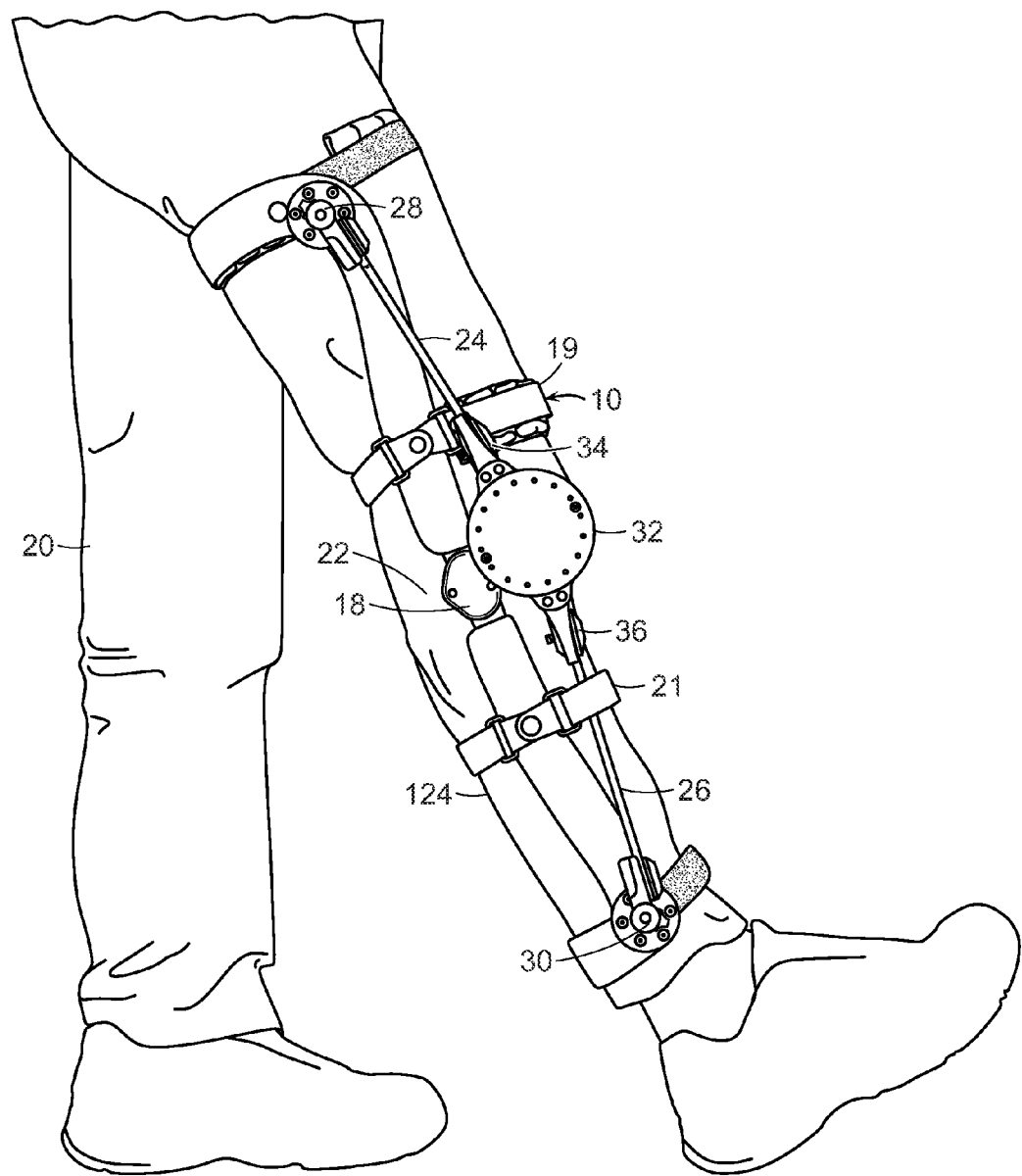
FIG. 3 is another side view of the exoskeleton shown in FIG. 1 at heel strike by a subject.
Figure 4:
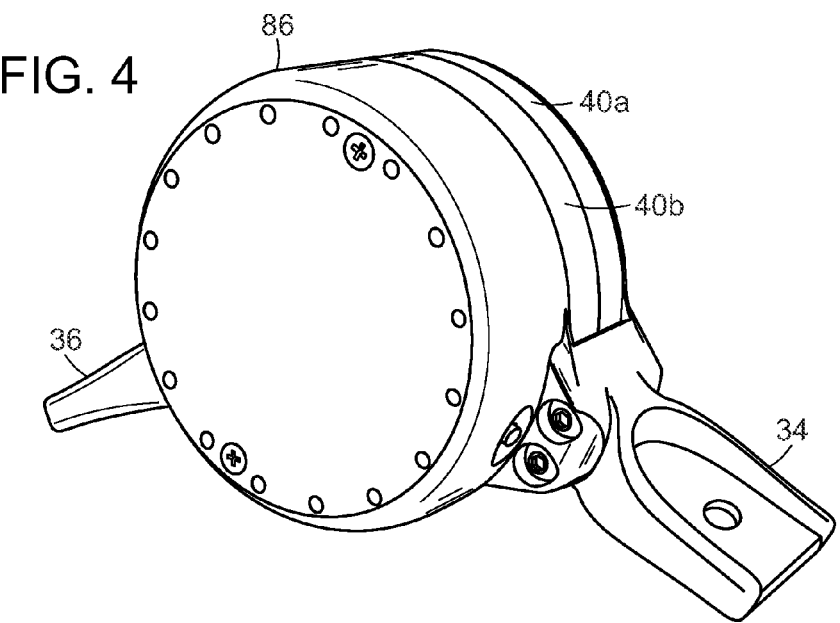
FIG. 4 is a perspective view of one embodiment of a left rotary clutch (for a left knee) of the invention.

One particular embodiment of a clutched elastic element exoskeleton is shown in FIGS. 1-3. As shown therein, exoskeleton 10 includes longitudinal harness 12. Longitudinal harness 12 includes proximal component 14 and distal component 16 hinged to proximal component 14. Longitudinal harness 12 can be formed of, for example, suitable conventional components, such as leather, laminate polymer composites, etc. Hinges 18 link a distal end of proximal component 14 to a proximal end of distal component 16 on either side of longitudinal harness 12. When fitted to a subject, such as a human, as shown in FIGS. 2 and 3, the axes of rotation of hinges 18 (not shown in FIG. 2) of exoskeleton 10 will typically be polycentric with motion compatible with that of knee 22 of subject 20. Alternatively, in an embodiment not shown, proximal component 14 and distal component 16 do not need to be hinged, other than by virtue of elastic elements 24,26 and clutch 32. Straps 19,21 about the thigh and calf of subject 20 stabilize proximal component 14 and distal component 16, respectfully, during use.

Proximal elastic element 24 and distal elastic element 26 are connected to proximal component 14 and distal component 16, respectively, of longitudinal harness 12 at proximal hinge 28 and distal hinge 30. Hinges 28,30 rotate about respective axes that are substantially parallel to an axis of rotation of knee 22.

Suitable elastic elements typically are of a type known to those in the art and include, for example, at least one member selected from the group consisting of leaf springs, compression springs and tension springs. As shown in FIGS. 1-3, proximal elastic element 24 and distal elastic element 26 are leaf springs. Leaf springs 24,26 are formed of a suitable material, such as is known in the art, including, for example, fiber glass and carbon fiber.

Figure 6:
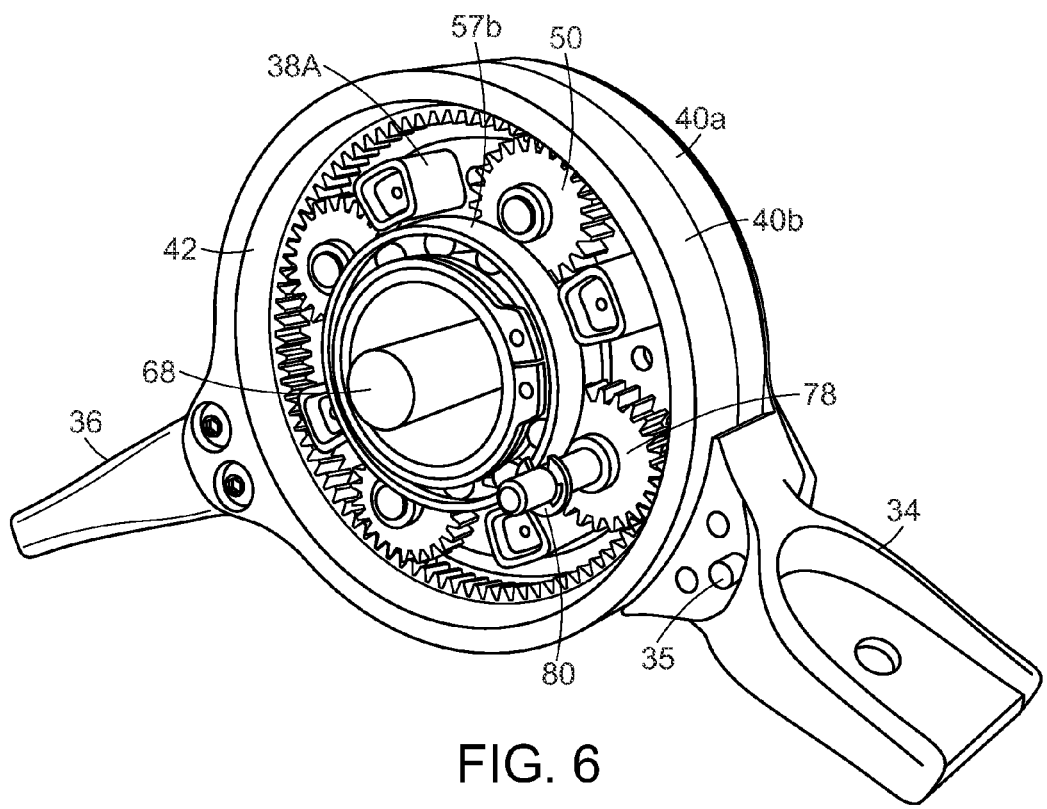
FIG. 6 is a perspective view of a portion of the interior of the rotary clutch of FIG. 4 showing the ring gear, planet gears, sun bearing and translating clutch plate.
Figure 7:
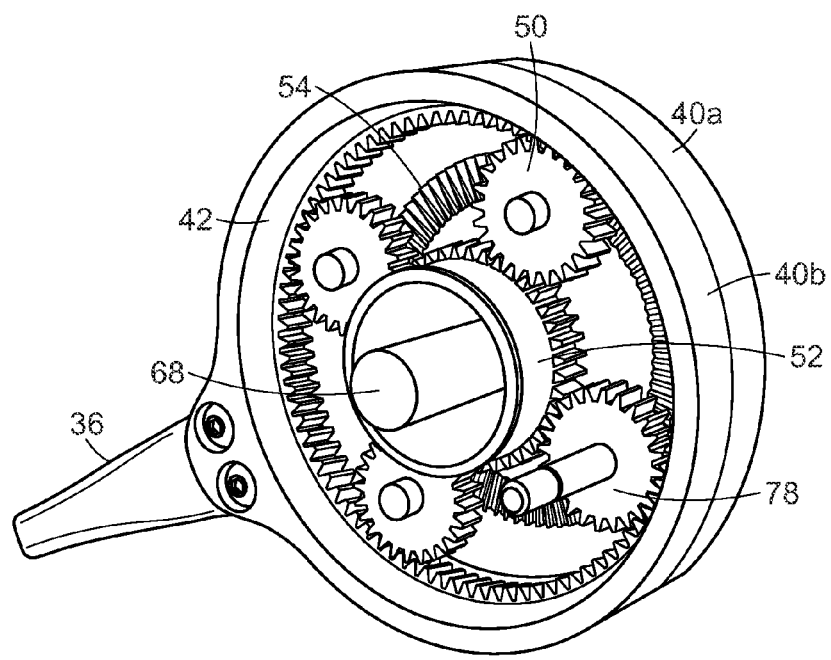
FIG. 7 is a perspective view of a portion of the interior of rotary clutch of FIG. 4 showing the ring gear, planet gears, sun gear and rotating clutch plate.
Figure 10:
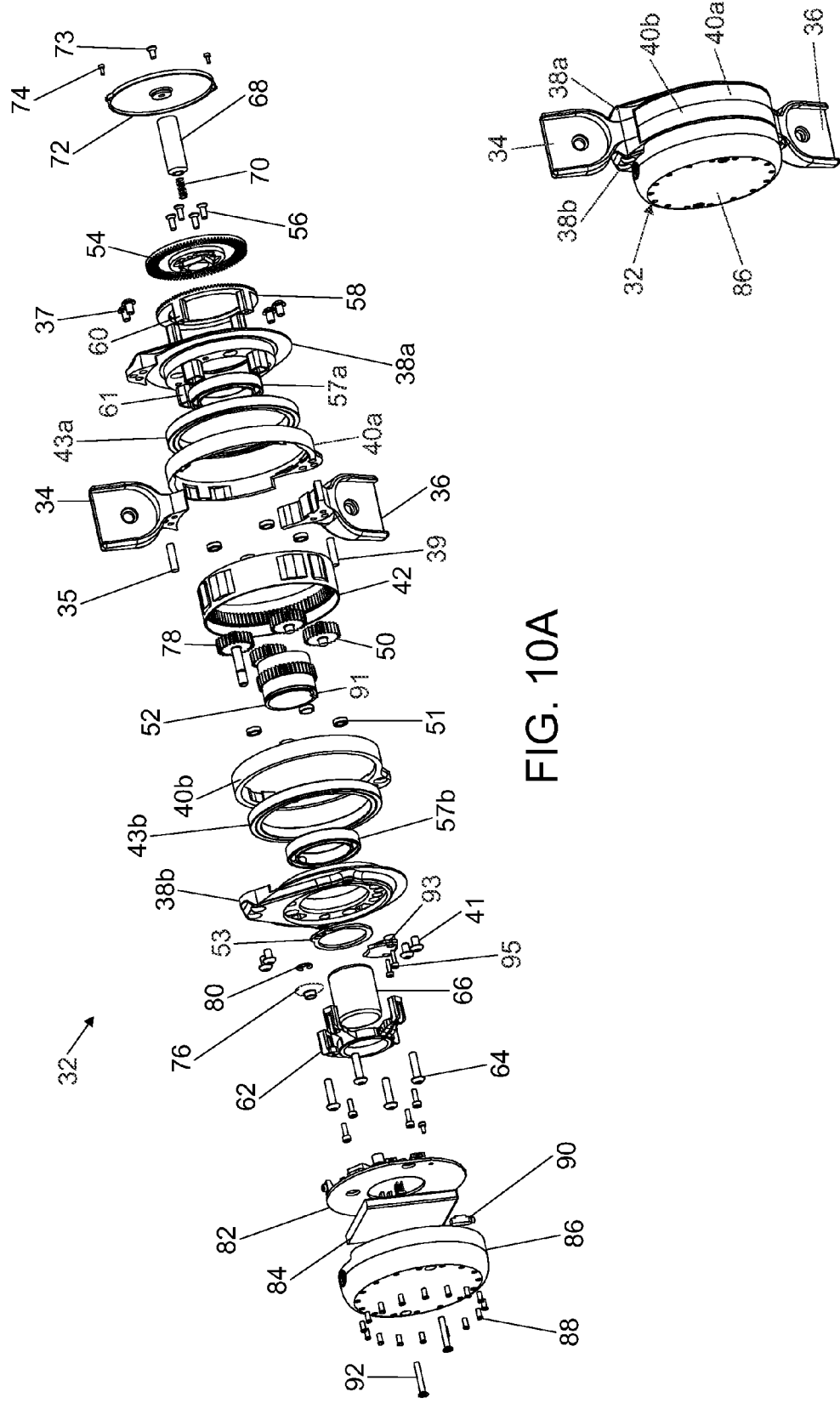
FIG. 10A is an exploded view of one embodiment of a right rotary clutch (for a right knee) of the invention.
FIG. 10B is a perspective view of the rotary clutch shown in FIG. 10A.
Figure 11:
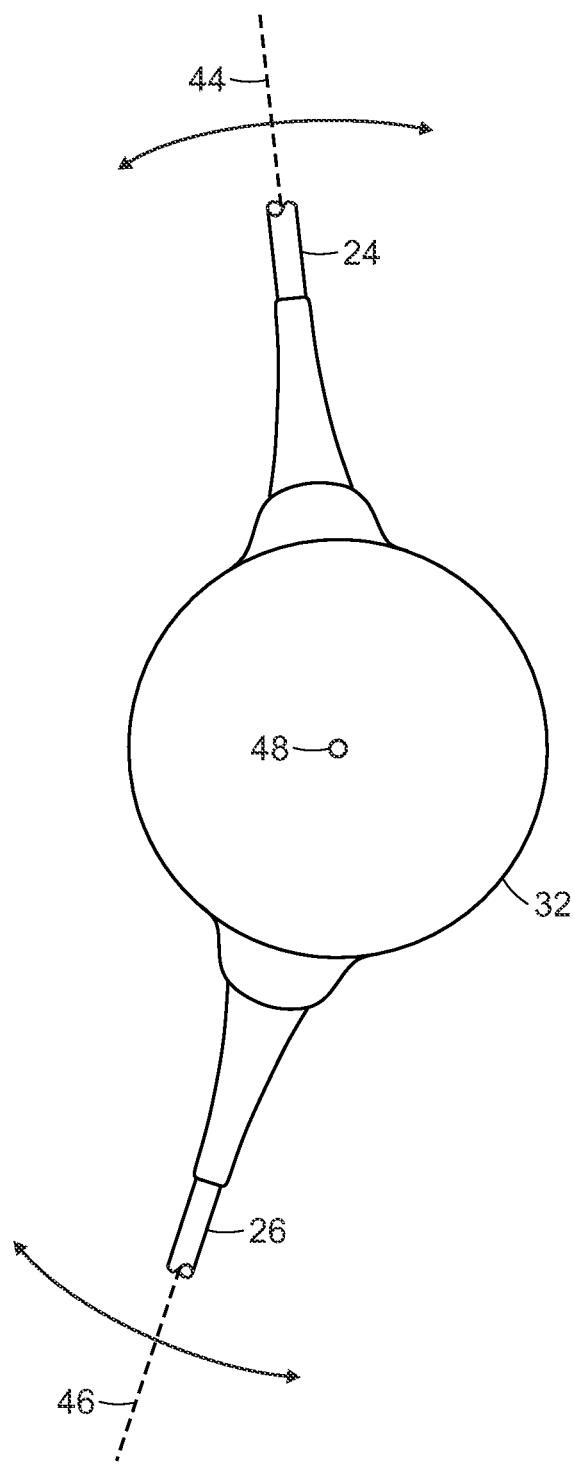
FIG. 11 is a side view, in part, of a rotary clutch of the invention with leaf springs extending therefrom.

Proximal leaf spring 24 and distal leaf spring 26 are linked by rotary clutch 32. Rotary clutch 32 is linked to proximal leaf spring 24 and distal leaf spring 26 at proximal mount 34 and distal mount 36, respectively. As can be seen in FIGS. 6 and 10A, proximal mount 34 is attached to medial housing 38a and lateral housing 38b by pin 35 and screws 37. Distal mount 36 is fixed to distal ears 40a,40b and ring gear 42 by pin 39 and screws 41. As can be seen in FIG. 11, major longitudinal axes 44,46 of proximal and distal leaf springs 24,26 extend through and are rotatable about central axis 48, or center of rotation, of rotary clutch 32.

Returning to FIGS. 4-10B, distal ears 40a, 40b secure ring gear 42 that, in turn, directs rotation of planet gears 50,78 and sun gear 52 which reside within ring gear 42. Planet gears 50,78 are stabilized by planet bearings 51. Sun gear 52 is fixed to rotating clutch plate 54 by flathead screws 56 and stabilized by sun bearing 57b. Ring gear 42, planet gears 50,78 and sun gear 52 preferably are formed of a suitable material, such as titanium.

Ball bearings 57a, 57b support rotating clutch plate 54 and sun gear 52. Retaining ring 53 retains sun gear 52 in position relative to bearing 57b. Sun gear 52 is hollow, allowing solenoid 66, which actuates the clutch, to be placed within sun gear 52. Radial and axial forces are borne by a pair of opposing angular contact ring bearings 43a,43b which support distal ears 40a,40b and ring gear 42. Medial housing 38a includes linear plain bearings 61 which support translating clutch plate 58 and are located between the planetary gears 50,78 (See FIG. 6).

Translating clutch plate 58 includes legs 60 that extend through medial housing 38a and are fixed to solenoid mount 62 by screws 64. Rotary clutch plate 54 and translating clutch plate 58 preferably are formed of a suitable material, such as titanium. Other remaining components of rotary clutch typically are formed of a suitable material known in the art, such as aluminum. Solenoid 66 is fixed to solenoid mount 62 and extends in non-interfering relation through sun gear 52 to solenoid plunger 68. Solenoid return spring 70 biases solenoid plunger 68 away from solenoid 66. Solenoid plunger 68 is rigidly fixed by screw 73 to medial cap 72 which, in turn, is fixed to medial housing 38a by screws 74. Optical encoder disk 76 is fixed to long planet gear 78 by E-clip 80. Circuit board 82 and lithium ion battery 84 are fitted within lateral cap 86. Light pipes 88 and right angle light pipe 90 are also fitted at lateral cap 86. Right angle light pipe 90 is employed to indicate that the device is on, light pipes 88 are employed for diagnostic purposes. Lateral cap 86 is fixed to lateral housing 38b by flathead screws 92. Hard stop 93 is secured to lateral housing 38b by screws 95, as shown in FIG. 10A, and is employed to prevent both hyperextension and collision of mounts 34,36. To this end, hard stop 93 may be engaged on either side by a tab 91 (FIG. 10A) protruding from sun gear 52.

As can be seen in FIG. 11, upon actuation, solenoid 66 will draw plunger 68 within solenoid 66 in a direction opposite that of bias provided by solenoid-return spring 70. Solenoid mount 62, in turn, is directed by movement of solenoid 66 along plunger 68 that moves translating clutch plate 58 into mating relation with rotating clutch plate 54. Engagement of translating clutch plate 58 with rotating clutch plate 54 by actuation of solenoid 68 causes rotation of rotating clutch plate 54 consequent to rotation of planetary gears 50,78 to stop, thereby preventing further rotation of distal mount 36 relative to proximal mount 34 about a central axis of rotary clutch 32. Terminating actuation of solenoid 66 causes plunger 68 to move outwardly from within solenoid 66 by virtue of bias provided by solenoid return spring 70, thereby causing translating clutch plate 58, which is slidably engaged with medial housing 38a, to move away from rotating clutch plate 54, thereby disengaging translating clutch plate 58 from rotating clutch plate 54 and restoring freedom of rotation of distal mount 36 about a central axis of rotary clutch 32 relative to proximal mount 34.

Figure 5:
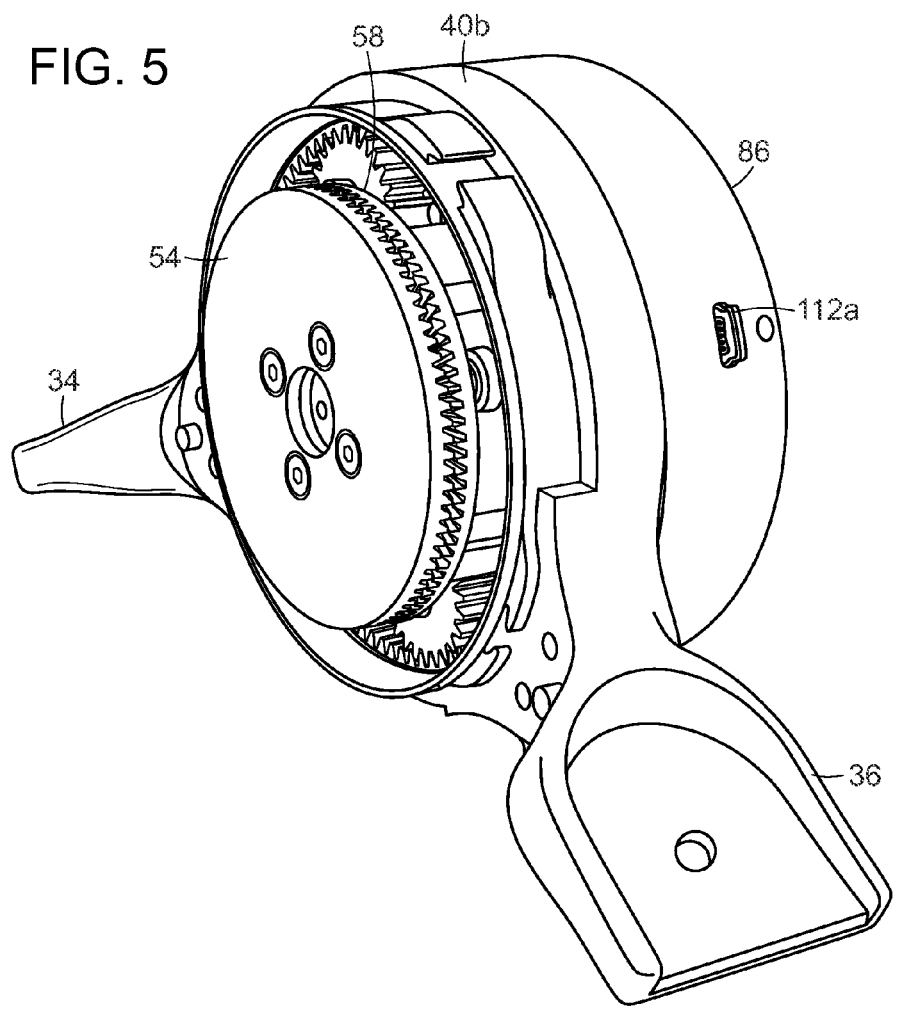
FIG. 5 is a perspective view of a portion of an interior of the left rotary clutch showing the rotary clutch plate and translating clutch plate.

As can be seen in FIGS. 9 and 9A, and in FIG. 5, teeth 94 of translating clutch plate 58 and rotating clutch plate 54 preferably have a mating sawtooth, rather than a square tooth, or castle, configuration in order to facilitate alignment during relative movement of the translating and rotating clutch plates 58,54. Further, the sawtooth configuration typically is asymmetric, as shown in FIG. 9A, with the leading edge having an angle, for example, of exactly or very nearly 90 degrees in order to maximize holding tongue.

Figure 13:
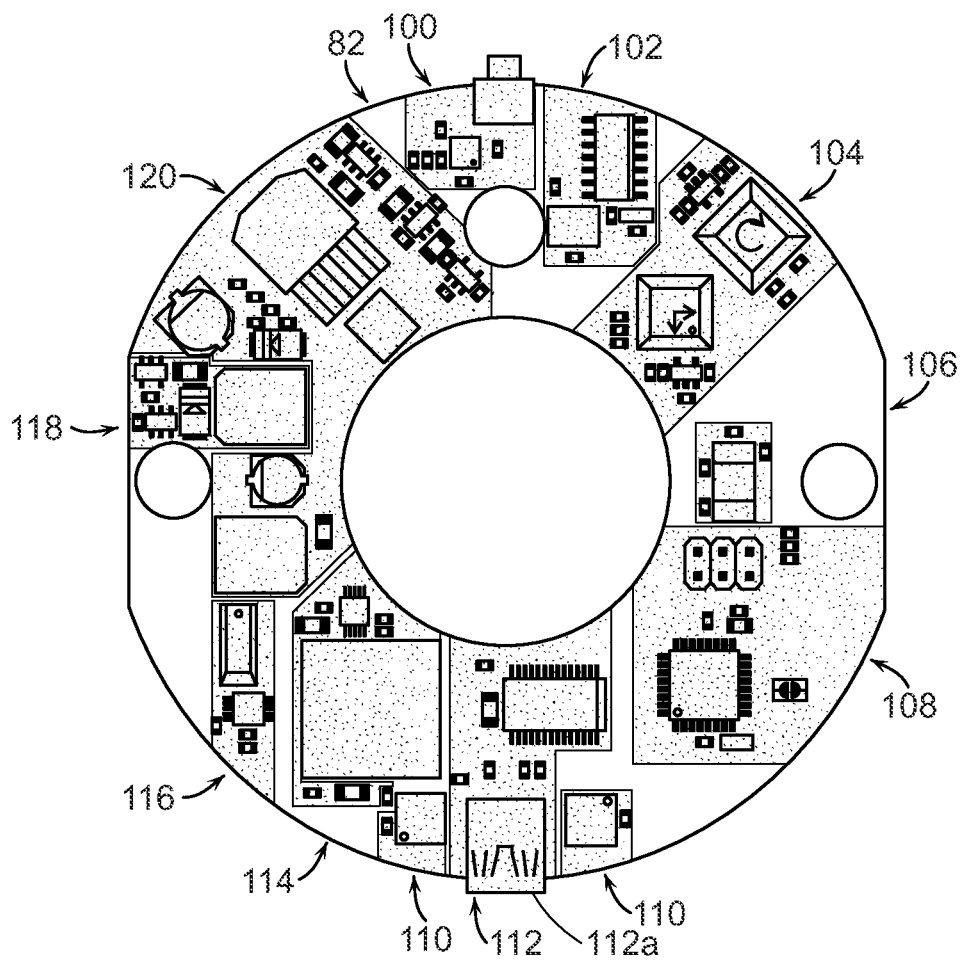
FIG. 13 is a plan view of one embodiment of a circuit board employed by a rotary clutch of the invention.

Circuit board 82 is powered by lithium-ion battery 84 (FIG. 10A) and includes, as can be seen in FIG. 13, battery protection unit 100, reflective optical encoder 102, inertial measurement unit 104, optical break-beam 106, microcontroller 108, light emitting diode (LED) drivers 110, USB interface 112, micro SD card 114, real-time clock 116, solenoid driver 118, and switching power supply 120. Battery protection unit 100 modulates battery charging and monitors for potentially hazardous battery conditions. Inertial measurement unit 104 includes a gyroscope and an accelerometer that are employed as secondary gait sensors. Solenoid drive 118 is an electronic circuit that provides current to solenoid 66 (FIG. 10A). Reflective optical encoder 102 is a sensor that is employed to determine angular position of rotary clutch 32 (FIG. 10A). Optical break-beam 106 is a sensor employed to determine position of solenoid 66 (FIG. 10A). Microcontroller 108 is the main computer processor of rotary clutch 32 (FIG. 10A). LED drivers 110 are electronic circuits that provide current to diagnostic LEDs that transmit light to the outside of the lateral cap. USB interface 112 is an electronic circuit employed to transmit detailed diagnostics and logs over USB connector 112a, shown in FIG. 5 and FIG. 13, and is also employed to reprogram microcontroller 108, as necessary. Micro SD card 114 is employed as memory to store logs. Real-time clock 116 is an electronic circuit employed to keep time, even when rotary clutch 32 (FIG. 10A) is not in use, to thereby accurately time-stamp logs. Switching power supply 120 is an electronic circuit which regulates voltage to acceptable levels for various components.

When in use, proximal component of longitudinal harness is strapped to thigh member 122 of the subject 20, such as a human subject, as shown in FIGS. 2 and 3. Distal component 16 is strapped to a lower leg, such as below calf 124 of subject 20. Hinges 18 transversely span knee 22 of subject 20. The axes of rotation of hinges 18 are generally polycentric consistent with knee 22.

Figure 14G:
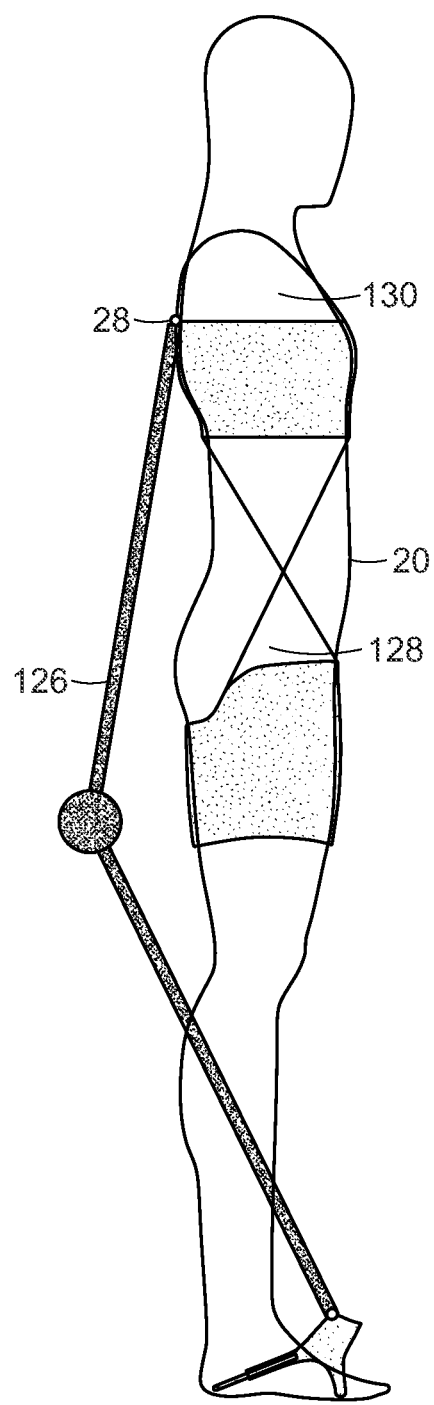
FIG. 14G is a schematic illustration of an example embodiment of an exoskeleton of the invention employing a rotary clutch and having a posterior configuration.

As shown in FIGS. 14A-14C, in alternate embodiments, proximal component 126 can be fitted to hip 128 of subject 20, whereby hinge 28 at proximal component 126 can be co-axial or polyaxial relative to hip 128 of subject 20. In still another embodiment, shown in FIGS. 14D-14F, proximal component 126 is fixed to torso 130 or chest of subject 20, whereby hinge 28 at proximal component 126 is above the axis of rotation of hip 128, and proximal leaf spring 24 spans hip 128 of subject 20. As shown in FIGS. 14A-14C proximal component 126 is fixed at or below hips 128 of subject 20, while distal component 134 is fixed at or below ankle 132 of subject, whereby clutched elastic element exoskeleton 10 spans one, two or three of ankle 132, knee 22 and hip 128 joints of subject 20. In another embodiment (FIGS. 14E-14F), clutched elastic element exoskeleton 10 spans all three of ankle 132, knee joint 22 and hip joint 128. FIG. 14G shows an embodiment that has a posterior configuration and which is a variant of the embodiment of FIG. 14F. As shown, the proximal component 126 is fixed to a posterior or back of torso 130 of subject 20. FIGS. 15A-15E show various harnesses that can be employed to support hinge 28 at proximal component 126 to subject 20 at or above hip 128.

Figure 16A:
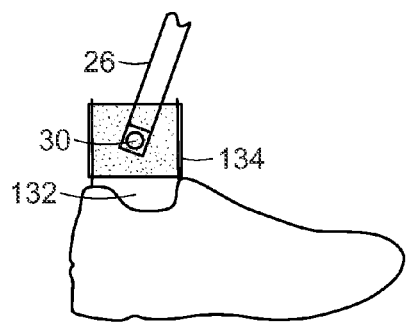
FIGS. 16A through 16E are schematic representations of various exemplary embodiments of mechanisms for mounting distal portions of exoskeletons of the invention to a subject.
Figure 16B:
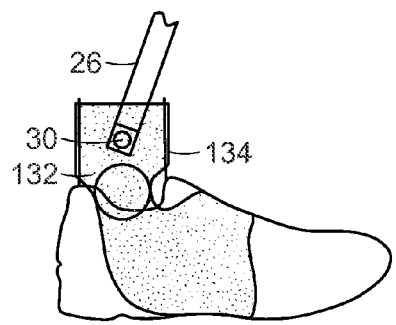
Figure 16C:
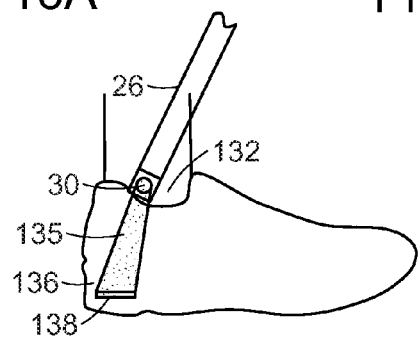

In other embodiments, shown in FIGS. 16A-16E, distal component 134 can be fitted to subject 20 at or below the ankle 132. For example, as shown in FIGS. 16A-16B, where the distal component 134 is fitted at ankle 132, hinge 30 can be can be fixed to the shin so that spring 26 is not affected by rotation of ankle 132. In one embodiment, shown in FIG. 16C, distal component 135 can include rigid attachment 138 attached at heel 136 of subject 20, with an offset to be approximately concentric to ankle 132 so that the spring effectively does not span the ankle. In other embodiments, shown in FIGS. 16D-16E, where distal components 137, 141, respectively, are fitted below ankle 132, distal leaf spring 26 effectively spans ankle 132. In the embodiments shown in FIGS. 16A-16C, motion of spring 26 is isolated from rotation of ankle 132, either by attaching to shin (FIGS. 16A-16B) or by attaching to foot (FIG. 16C) and placing a pivot point (e.g., hinge 30) very near the axis of the ankle to minimize the effective moment arm. In the embodiments shown in FIGS. 16D-16E, in contrast, movement of ankle 132 causes movement of spring 26.

Figure 16D:
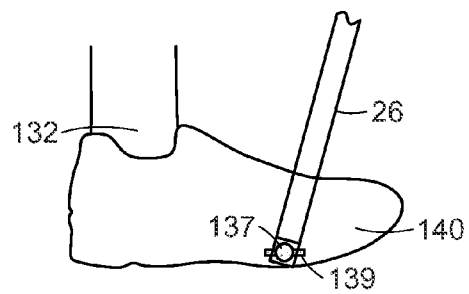

In one embodiment, shown in FIG. 16D, distal component 137 includes rigid attachment 139 at toe 140 of the subject 20. This embodiment forces subject 20, when running, to lead with toe 140 on ground strike of subject 20. This embodiment is particularly useful for augmented hopping.

Figure 16E:
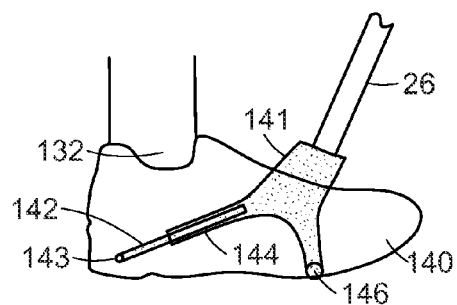

In still another embodiment, shown in FIG. 16E, two degrees of freedom are provided at the point of contact between distal component 141 and the subject. In this embodiment, direct ground contact is permitted independent of foot position, thereby allowing normal heel strike and toe-off while loading directly into the ground during running. Specifically, longitudinal movement is permitted between pin 142, fixed at heel 143, and holster 144 of distal component 141, and rotational movement is permitted about pivot point 146 of distal component 141.

Figure 17A:
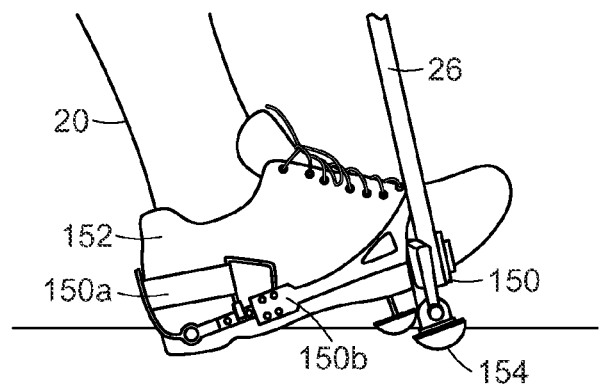
FIGS. 17A through 17C are schematic representations of one exemplary mechanism for mounting an exoskeleton to a foot of a subject and the position of that mechanism during a stance phase of a stride of the subject.
Figure 17B:
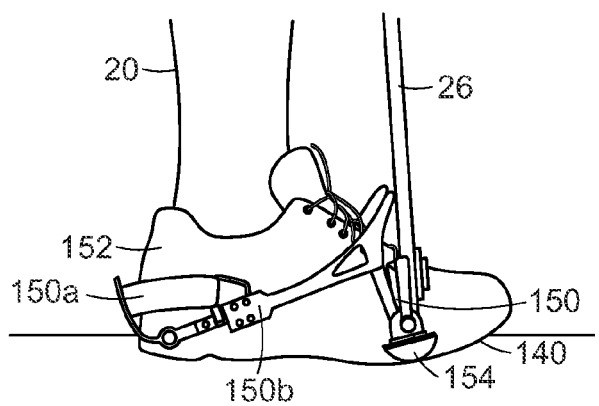
Figure 17C:
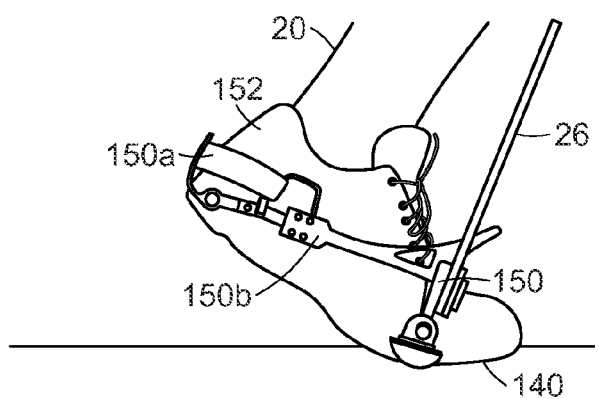

One specific embodiment of the schematic representation of FIG. 16E is shown in FIGS. 17A-17C, whereby articulated distal attachment 150 allows spring 26 to load through the ground even as foot 152 moves around it. Return springs 150a and 150b are located at the heel of the subject and along a linear bearing in the attachment, respectively. At heel-strike, spring 26 contacts ground below toe 140. As foot 152 rolls forward, linear and rotary joints allow spring contact point 154 to remain stationary until toe-off, after which return springs 150a and 150b contract, resulting in movement of the device back to the position shown in FIG. 17A.

During use, elastic element exoskeleton 10, shown in FIGS. 2 and 3, is fixed at proximal component 14 of longitudinal harness 12 to thigh 122 of subject 20 and at distal component 16 to lower leg 124 of subject 20 above ankle joint 132. Microcontroller 108 (FIG. 13) of rotary clutch 32 adaptively modulates anticipation of maximum extension of rotary clutch 32 while subject 20 is running. The term "adaptively modulating anticipation" is also referred to, and has the same meaning as "adaptively anticipating". In one embodiment, adaptively modulating antici-pation of (i.e., adaptively anticipating) maximum leg extension of rotary clutch 32 includes measuring the angular position of the rotary clutch 32 by use of optical encoder 106 (FIG. 13) of rotary clutch 32, and the angular velocity of rotary clutch 32 in a sagittal plane in subject 20 by use of gyroscope of inertial measurement unit 104 (FIG. 13). The angular position of rotary clutch 32 and angular velocity of exoskeleton 10 are correlated with a phase of the gait cycle of subject 20 while running, to thereby predict the time of maximum extension of rotary clutch 32 during late swing phase of the gait cycle of subject 20, prior to leg strike of subject 20, while running. Further, adaptively modulating anticipation of maximum leg extension of rotary clutch 32 can include, upon or after estimating predicted maximum leg extension, correlating past positions of the rotary clutch 32 during terminal swing phase with each other, to thereby predict maximum extension of rotary clutch 32 while subject 20 is running.

Figure 18A:
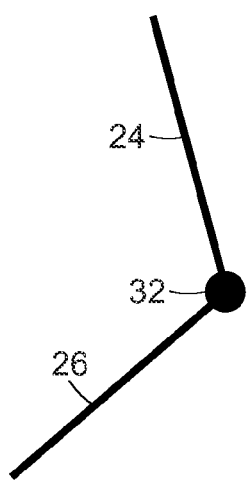
FIGS. 18A through 18C are schematic representations of positions of the exoskeleton of the invention in late swing, heel strike and stance positions during running.
Figure 18B:
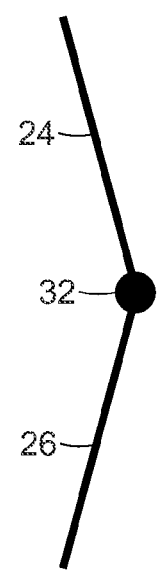
Figure 18C:
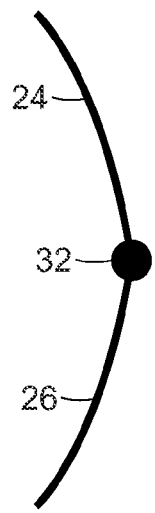

FIGS. 18A-18C depict compression of leaf springs 24 and 26 before and during the stance phase of running, while rotary clutch 32 is locked. As shown in FIG. 18A, rotary clutch 32 has not yet reached maximum extension in late swing phase. In FIG. 18B, rotary clutch 32 has reached maximum extension and has locked essentially simultaneously with knee strike. As can be seen in FIG. 18C, during stance phase, linear springs 24 and 26 store potential energy by flexing. The stored potential energy is released during late stance phase to thereby augment running by the subject.

Optionally, rotary clutch 32 is disengaged by correlating the position of exoskeletal and angular velocity of exoskeleton 10 with a mid-stance or terminal stance phase of the gait cycle while subject 20 is running, and actuating disengagement of the rotary clutch 32 at mid-stance phase, as predicted by the correlation.

Figure 23:
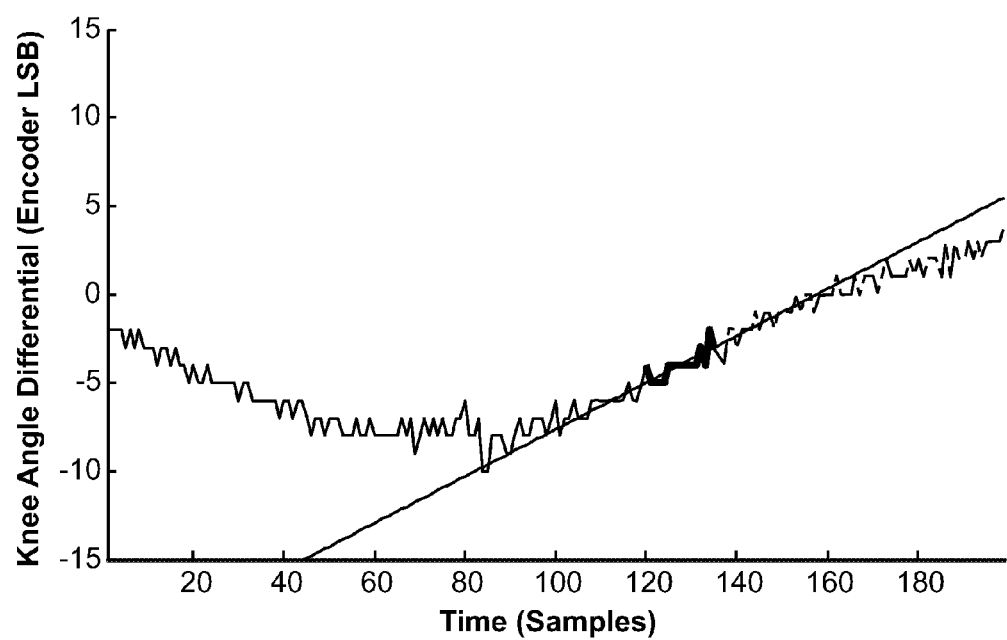
FIG. 23 is another depiction of the simulation described with respect to FIG. 22.

As a further option, correlating past positions of rotary clutch 32 to predict maximum extension of the rotary clutch is conducted by applying a latency compensation algorithm. In one embodiment, the latency compensation algorithm includes a quadratic least squares analysis. In an alternate embodiment, the latency compensation algorithm includes fitting differentials of encoder readings to a line and seeking a zero crossing, as shown in FIG. 23, and described below.

Figure 12:
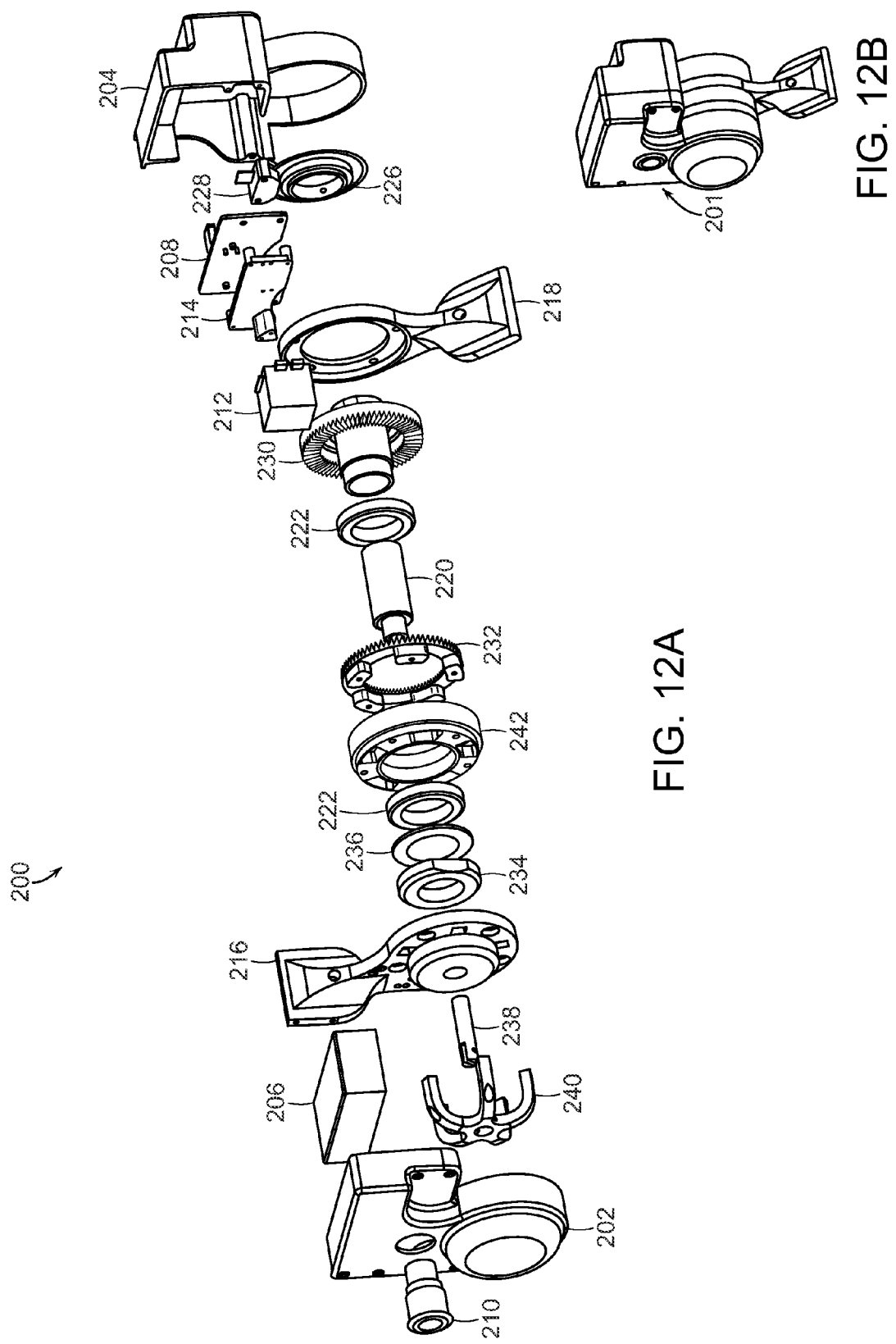
FIGS. 12A and 12B are exploded and perspective views, respectfully, of another embodiment of a rotary clutch of the invention, lacking a gear box.

In another embodiment, shown in FIG. 12A, clutch 200 lacks a gear box, such as the ring, planets and sun gear assembly of the embodiment shown in FIGS. 4-11. Rotary clutch 200, as shown, is a left knee clutch. Clutch housing 201 (FIG. 12B) includes lateral clutch housing 202 and medial clutch housing 204 (FIG. 12A). Lithium polymer battery 206 fits within lateral clutch housing 202 and medial clutch housing 204. Lithium polymer battery 206 is electrically connected to circuit board 208. Power button 210 extends through lateral clutch housing 202 and is linked to circuit board 208. Inertial measurement unit 212 is mounted to frame 214. Circuit board 208, in turn, is mounted within medial clutch housing 204. Proximal mount 216 is mounted to a linear spring (not shown), as described above. Distal mount 218 is mounted to distal linear spring (not shown) as also described above. Solenoid 220 extends through bearings 222, rotating clutch plate 230, distal mount 218 and encoder disc 226. Encoder disc 226 is fitted to encoder reader 228 which, in turn, is mounted within medial clutch housing 204 and electrically connected to circuit board 208. Rotating clutch plate 230 is fixed to proximal mount 216. Encoder disc 226 is fixed to distal mount 218 and rotates with distal mount 218. Solenoid 220 is fixed within rotating clutch plate 230. Translating clutch plate 232 is seated within housing 242. Preload nut 234 and belleville washer 236 are seated within housing 242. Preload nut 234 secures rotating clutch plate 230 in place while allowing rotation. Proximal mount 216 is fixed to housing 242. Solenoid plunger 238 is fixed to plunger mount 240 and extends through plunger mount 240, preload nut 234, belleville washer 236, and also extends within solenoid 220. Actuation of clutch 200 causes plunger 238 to move within solenoid 220, thereby directing plunger mount 240 to move translating clutch plate 232 into engagement with rotating clutch plate 230. As with the rotary clutch described above, translating clutch plate 232 and rotating clutch plate 230 are formed of a suitable material, such as titanium. A fully-assembled left knee clutch is shown in FIG. 12B. Actuation of clutch 200 is triggered in the same manner as described with respect to the clutch and the remainder of the exoskeleton shown in FIG. 1, described supra.

The following representation is an exemplary embodiment of the method of the invention as applied to one embodiment of the exoskeleton of the invention. The description and results set forth should not be considered limiting in any way.

EXEMPLIFICATION

Electronics and Instrumentation

To increase reliability and facilitate maintenance, the system is designed with a minimum number of routed wires. To this end, all electronics are packaged together within a cap-shaped subassembly which attaches to the lateral face of the proximal assembly and is easily removed for maintenance. This lateral subassembly contains a 2000 mAh lithium polymer battery cell and the circuit board, both fixed to a milled aluminum housing. The circuit board is annular, to accommodate the last 2 mm of solenoid travel through the center of the board. All sensors (Table 4-1) are mounted directly to the circuit board and, where necessary, interface optically to appropriate mechanical transducers within the clutch. Only a single pair of wires, connecting the solenoid to the circuit board, links the lateral assembly to the body of the clutch. A floorplan of the circuit board is shown in FIG. 13.

An AtMega168PA AVR microcontroller operating at 12 MHz controls the clutch, using a development framework described below. A set of sixteen LEDs, directed to the face of the lateral subassembly by light pipes, provides visual indication of state. More complete diagnostic logs are available through USB tethering or may be recorded on an onboard MicroSD card for later analysis. The microcontroller may be reprogrammed over USB.

A three degree of freedom inertial unit comprising a dual-axis MEMs accelerometer and a MEMs gyroscope provides acceleration and rotation rate sensing within the sagittal plane. The accelerometers are primarily used to assess heel strike. Because the circuit board is fixed to the proximal assembly, the gyroscope is indicative of hip rotational velocity and is used to assess midswing and midstance. Rotation rate in midswing is particularly informative as an indication of running velocity.

TABLE 1

Sensors used in the exoskeletal knee.

| Measurement | Part | Technology | Iterface | Resolution | Range | Bandwidth |
|---|---|---|---|---|---|---|
| Anterior-Posterior Acceleration Superior-Inferior Acceleration | ADIS16006 | MEMS Accelerometer | SPI | 0.038 m/s$^2$ | ±49 m/s$^s$ | 100 Hz |
| Sagittal Plane Angular Rate | ADIS16100 | MEMS Gyroscope | SPI | 1.12° | ±1380°/s | 185 Hz |
| Exoskeletal Knee Angle | E4P (Disk) AEDR (Reader) LS7336R (Counter) | Reflective Encoder | SPI | 0.068° | 0-135° | |
| Clutch Engagement Distance | EE-SX1109 | Break Beam | Analog | 0.1 mm | 0-2 mm | |

Rotation of the clutch is measured using a reflective optical encoder. The quadrature phase disk is mounted to one of the planets rather than directly to the distal subassembly, both to accommodate the solenoid at the center of the device and to obtain an effective increase in resolution from the higher speed of the planets. It aligns with the Printed Circuit Board (PCB)-mounted reader when the lateral subassembly is installed.

Solenoid position feedback is obtained from an infrared break beam sensor soldered to the PCB interacting with an aluminum flag machined into the solenoid mount. This flag is dimensioned such that the sensor saturates when the solenoid mount is completely disengaged, but provides analog sensing over the final 2 mm of engagement, including any partial tooth engagements. This sensor is non-linear and exhibits slight hysteresis. For practical purposes, it offers 0.1 mm resolution.

Three power rails are generated from the 3-4.2V battery supply by switching converters. A 3.3V rail, produced by a four switch buck-boost converter, powers all onboard logic and most sensors. A 5V rail, produced by a boost converter, is needed to power the optical encoder and gyroscope, as 3.3V variants are unavailable. Finally, a 24V rail, produced by a boost converter, is used to power the solenoid. A 3V low dropout linear regulator is placed between the 3.3V rail and the accelerometer to eliminate power supply ripple, to which this sensor is particularly sensitive. The battery is charged over USB and is protected in hardware from over-current, over-voltage, and under-voltage. To conserve battery, the system is powered down by software after a period of inactivity on all sensors.

TABLE 2

Typical power consumption of exoskeletal knee clutch.
VBatt power and switching converter efficiencies
are calculated assuming nominal 3.7 V battery.

(a) Electronics power on battery, 3.3 V, and 5 V rails

| | $V_{Batt}$ | 3.3 V | 5 V |
|---|---|---|---|
| Battery Management | 14 µA | | |
| Microcontroller | | 5 mA | |
| Accelerometer | | 1.5 mA | |
| Gyroscope | | | 7.1 mA |
| Encoder Reader | | 15 mA | 2.1 mA |

TABLE 2-continued

Typical power consumption of exoskeletal knee clutch.
VBatt power and switching converter efficiencies
are calculated assuming nominal 3.7 V battery.

| Encoder Counter | | 200 µA | |
|---|---|---|---|
| Optical Break Beam | | 8 mA | |
| Real Time Clock | 15 nA | 80 µA | |
| LED Drivers | | 390 µA | |
| Total Current | 14 µA | 30.2 mA | 9.2 mA |
| Total Power | 52 µW | 100 mW | 46 mW |

(b) Typical solenoid power on 24 V rail

| Closing Duty Cycle | 1.00 |
|---|---|
| Closing Power | 13 W |
| Closing Time | 28.6 ms |
| Closing Energy | 375 mJ |
| Holding Duty Cycle | 0.24 |
| Holding Power | 725 mW |
| Holding Time (Typ.) | 300 ms |
| Holding Energy (Typ.) | 330 mJ |
| Total Energy (Typ.) | 705 mJ |
| Stride Period (Typ.) | 1.3 s |
| Total Power (Typ.) | 540 mW |

(c) Total power drawn from battery

| Rail | $P_{load}$ | Efficiency | $P_{battery}$ |
|---|---|---|---|
| $V_{Batt}$ | 52 µW | 100% | 52 µW |
| 3.3 V | 100 mW | 82% | 122 mW |
| 5 V | 46 mW | 92% | 50 mW |
| 24 V | 540 mW | 79% | 685 mW |
| | | | 857 mW |

Optimal control of the exoskeletal knee joint produces full engagement at the time of maximum knee extension shortly before heel strike and full disengagement prior to toe off. Ideally, each exoskeletal knee achieves this independently and requires no extrinsic inputs. The controller is implemented within a framework developed with prosthetic and orthotic systems in mind. The control problem itself is divided into two primary components: analyzing the gait cycle using kinematic sensing and compensating for the electromechanical latency of the clutch. Additionally, a pulse and hold strategy is implemented to reduce power consumption in the solenoid once the clutch is fully engaged.

The control framework, written for the AVR AtMega*8 line of microcontrollers, provides synchronous read-out of all sensors and update of all output devices as well as diagnostic and remote control capabilities. In particular, it is designed so that the space accessible to an end user is both easy to develop in and relatively well sandboxed. As this framework provides all low-level functionality, discussion here focuses on the two primary components of the exoskeleton control problem: analyzing the gait cycle using kinematic sensing and compensating for the electromechanical latency of the clutch.

Figure 19A:
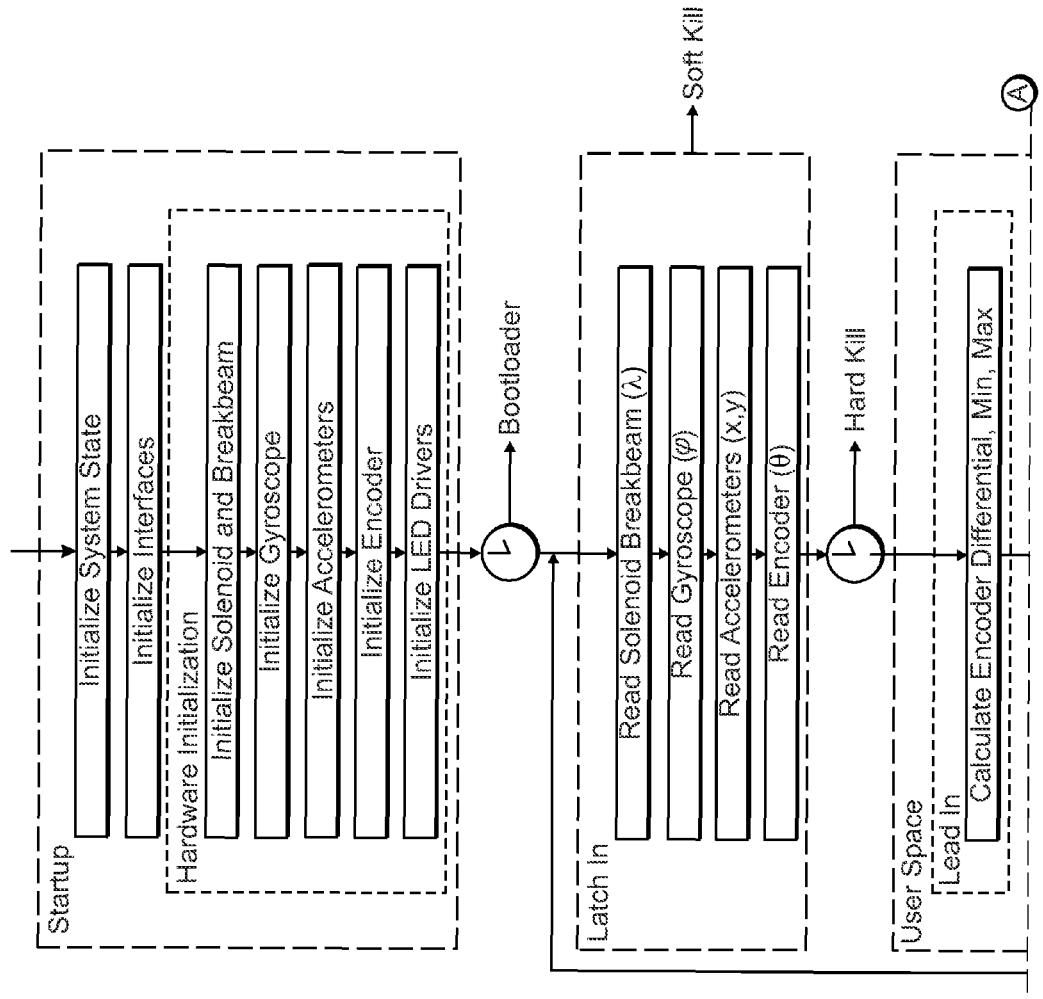
FIGS. 19A-19C depict program flow through the framework used to control the exoskeletal knee joint of the invention. The solenoid is activated during the doubly-circled states. Arrows exiting to the right indicate atypical paths, which at least briefly shut down the normal control loop. An interrupt (not shown) triggered by pressing the kill button causes an immediate soft kill.
Figure 19B:
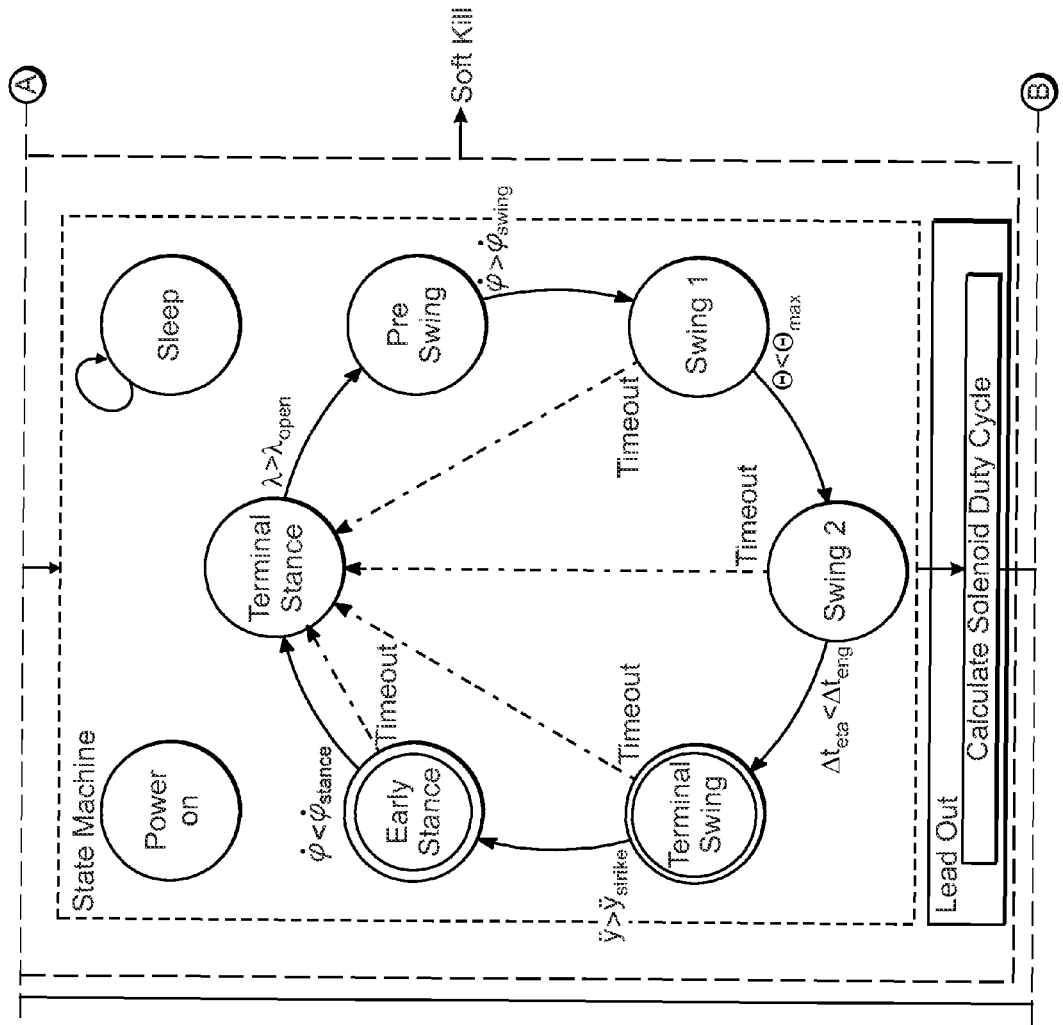
Figure 19C:
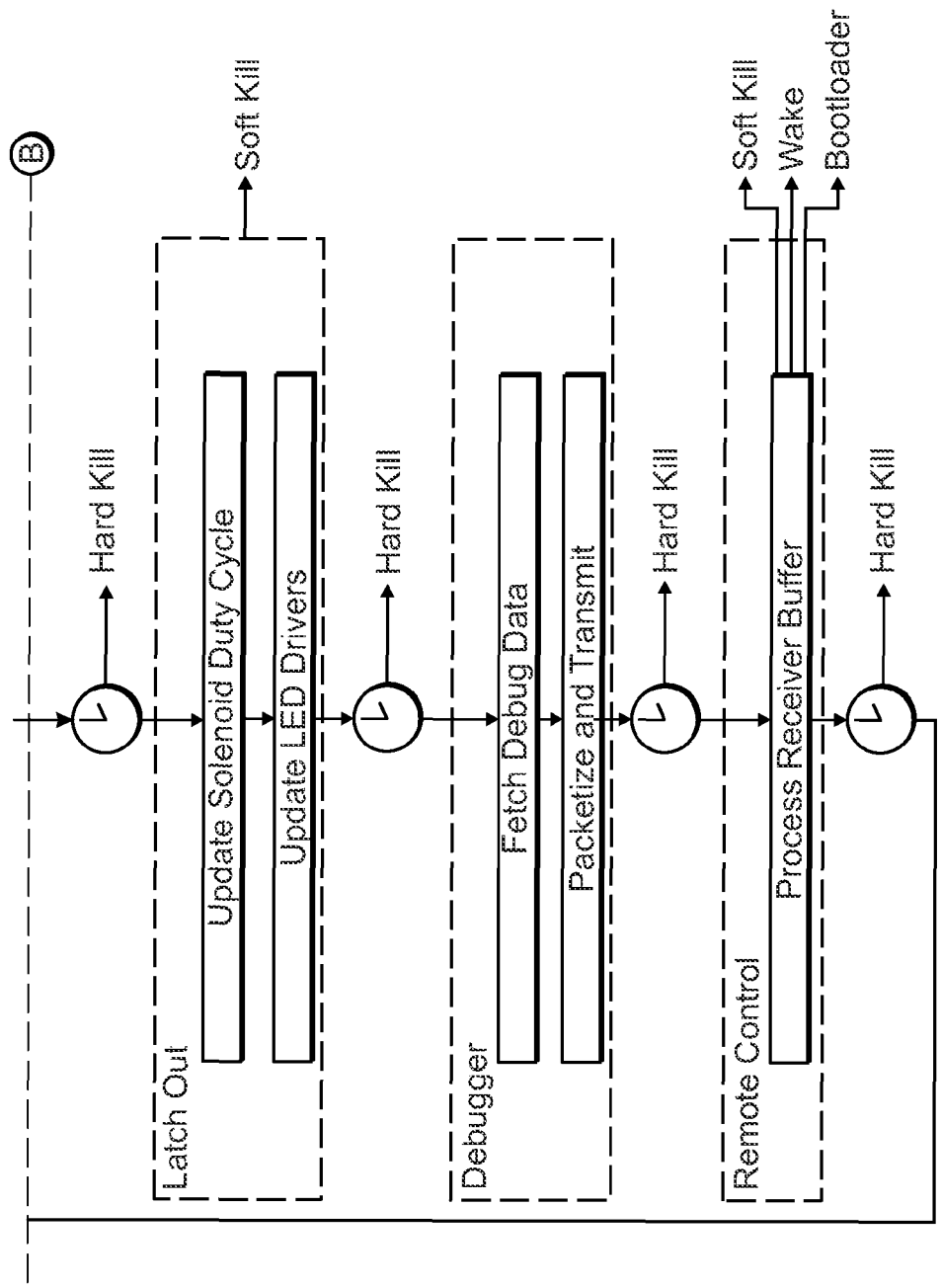

The framework, shown in FIGS. 19A-19C as configured for the exoskeletal knee clutch, implements synchronous time division for five phases of operation occurring in a loop:

Latch In: All input devices are read into memory.

User Space: A state machine is updated based on newly updated input data. Lead In and Lead Out subphases are executed immediately before and immediately after the state machine's update and are suited for filtering inputs and updating closed-loop controllers independently of the current state.

Latch Out: Changes made to output devices during the User Space phase are applied to hardware.

Debugger: A programmable set of data is logged, usually to USB or onboard memory.

Remote Control: A programmable set of memory locations may be updated, usually over USB. The remote control also provides for remote soft kill and wake as well as access to a bootloader so that new system code may be loaded.

Time division is enforced by a timer interrupt and a timeout results in an immediate hard kill, in which all potentially hazardous outputs are turned off and the system is shut down pending a reset from physical input or via the remote control. Program flow is blocked until the completion of a phase's time division if it completes early, guaranteeing synchronization at the start of each phase.

A soft kill, in which program flow continues, but potentially hazardous outputs are turned off and the state machine is forced into sleep, may be entered by pressing a kill switch, by software request during the Latch In, User Space, or Latch Out phases, or by request over the remote control.

Gait Analysis

Figure 20:
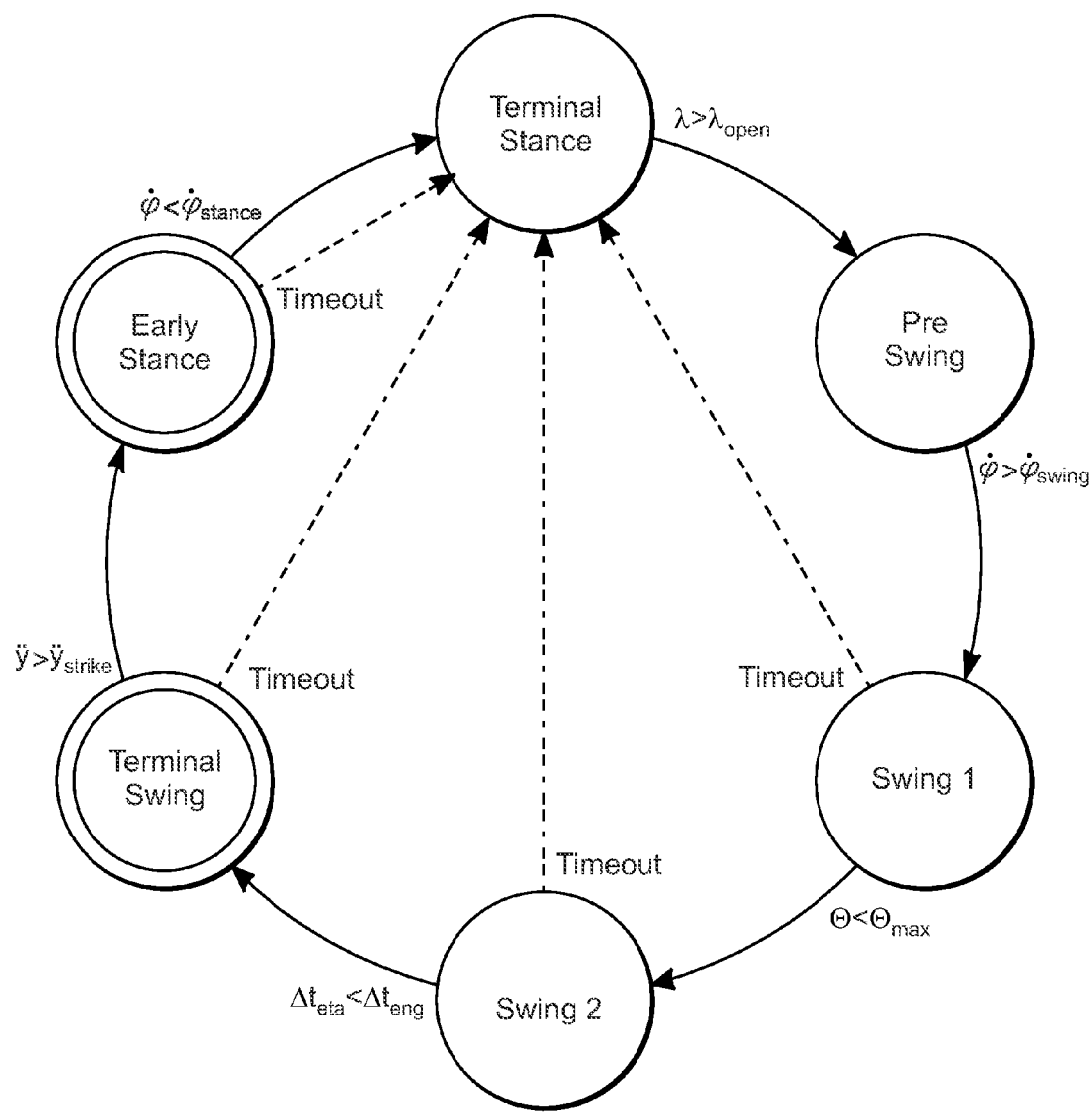
FIG. 20 is another depiction of the program flow of FIGS. 19A-19C.
Figure 21:
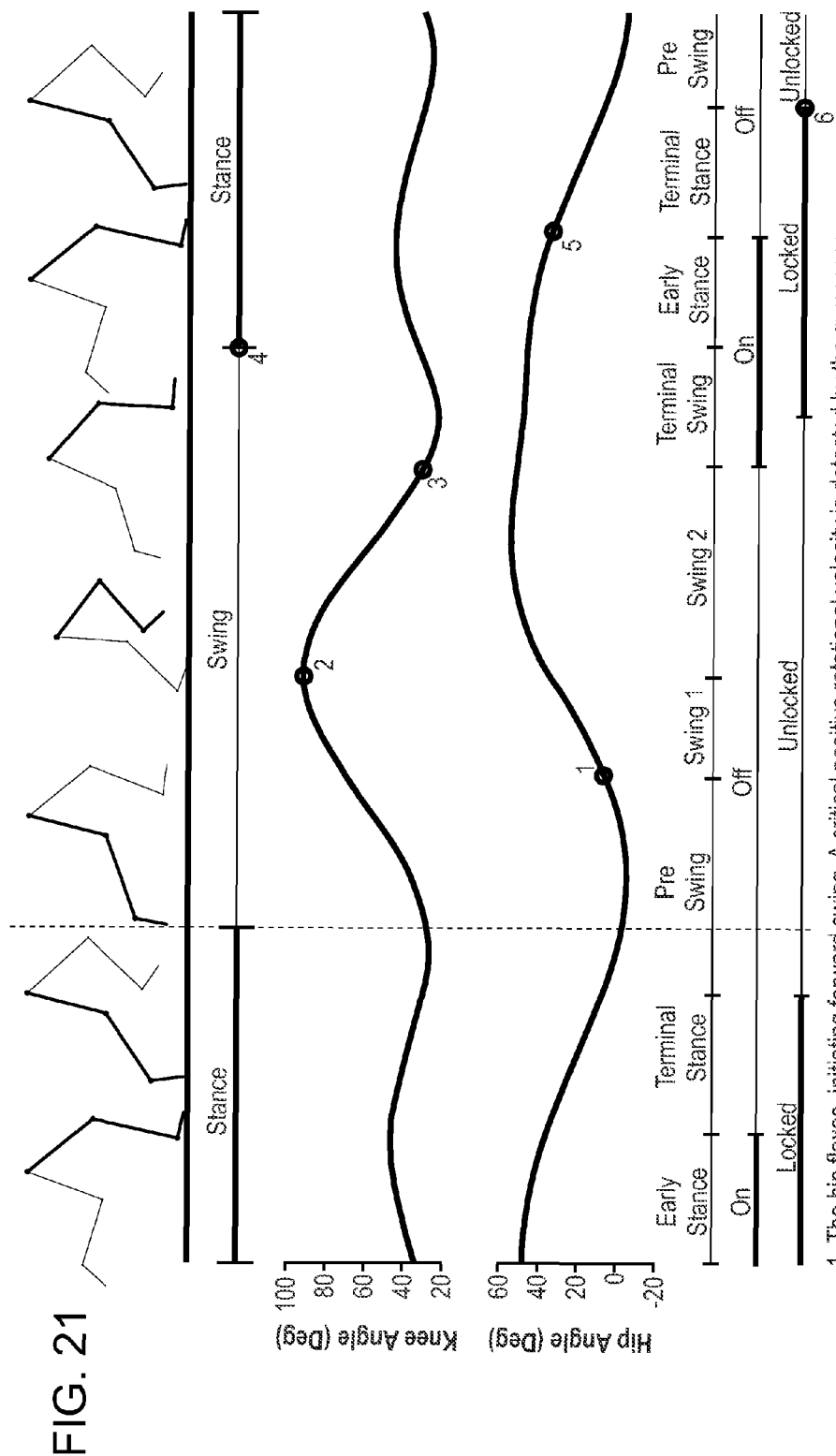
FIG. 21 is a depiction, in conjunction with FIG. 20, of events used to identify and act on phases of the gait cycle. Biological hip and knee data is stereotyped. More than one gait cycle is shown to clarify the periodic nature of this action.

The framework provides a user-friendly environment for implementing a gait analysis state machine. FIGS. 20 and 21 depict a stereotyped running gait, including knee and hip angles.

TABLE 3

Variables related to exoskeletal knee control, grouped into direct sensor readings and calculated internal state.

| Symbol | Description | Units |
|---|---|---|
| $\ddot{x}$ | Anterior-Posterior Acceleration | m/s² |
| $\ddot{y}$ | Superior-Inferior Acceleration | m/s² |
| $\dot{\psi}$ | Sagittal Plane Angular Velocity | °/s |
| $\theta$ | Exoskeletal Knee Angle | ° |
| $\lambda$ | Scaled Optical Break Beam Reading | |
| $\Delta t_{state}$ | Time Since Last State Change | ms |
| $\Delta t_{eta}$ | Predicted Time to Peak Knee Extension | ms |
| $\eta$ | Fractional Clutch Engagement | |

TABLE 4

Constants related to exoskeletal knee control, grouped into intrinsic hardware properties, tunable parameters, and tunable state machine time constraints

| Symbol | Description | Value |
|---|---|---|
| f | Update Frequency | 750 Hz |
| $\Delta t_{eng}$ | Clutch Engagement Time | 30 ms |
| $\lambda_{open}$ | Optical Break Beam Open Threshold | 0.20 |
| $\lambda_{closed}$ | Optical Break Beam Closed Threshold | 0.90 |
| W | Latency Compensation Window Size | 32 |
| $\dot{\psi}_{swing}$ | Sagittal Plane Angular Velocity Swing Threshold | 190°/s |
| $\dot{\psi}_{stance}$ | Sagittal Plane Angular Velocity Stance Threshold | −28°/s |
| $\ddot{y}_{strike}$ | Superior Acceleration Heel Strike Threshold | 17.2 m/s² |
| $\Delta\theta_{flexion}$ | Hysteresis Width to Detect Peak Knee Flexion | 2° |
| $\Delta\theta_{swing}$ | Minimum Knee Excursion in Swing | 44° |
| $D_{open}$ | Solenoid Duty Cycle While Closing | 1.00 |
| $D_{closed}$ | Solenoid Duty Cycle Once Closed | 0.24 |
| $\Delta t_{Swing1, max}$ | Maximum Time in Swing 1 | 200 ms |
| $\Delta t_{Swing2, max}$ | Maximum Time in Swing 2 | 320 ms |
| $\Delta t_{TerminalSwing, max}$ | Maximum Time in Terminal Swing | 120 ms |
| $\Delta t_{EarlyStance, min}$ | Minimum Time in Early Stance | 40 ms |

TABLE 4-continued

Constants related to exoskeletal knee control, grouped into intrinsic hardware properties, tunable parameters, and tunable state machine time constraints

| Symbol | Description | Value |
|---|---|---|
| $\Delta t_{EarlyStance, max}$ | Maximum Time in Early Stance | 200 ms |
| $\Delta t_{TerminalStance, min}$ | Minimum Time in Terminal Stance | 20 ms |

Relying exclusively on the onboard sensor measurements introduced in Table 1, a simple state machine (shown in FIG. 20) suffices to interpret the phases of this gait:

1. Preswing: Toe-off completes, the knee flexes in order to minimize its moment of inertia for forward swing, and the hip begins to flex accelerating the leg forward. Positive rotation of the gyroscope exceeding $\dot{\psi}_{swing}$ causes transition to Swing 1.
2. Swing 1: The knee continues to flex, eventually achieving maximum flexion. Once the exoskeletal knee angle has extended beyond its observed maximum flexion by a hysteresis band $\Delta\theta_{flexion}$, the state machine advances to Swing 2.
3. Swing 2: The knee begins to extend in preparation for heel strike. The solenoid latency compensation algorithm is activated. Once the projected time to maximum knee extension $\Delta t_{eta}$ is less than the known clutch engagement time $\Delta t_{eng}$ and the exoskeletal knee angle has decreased by at least $\Delta\theta_{swing}$, the solenoid is activated and the state machine progresses to Terminal Swing.
4. Terminal Swing: The clutch engages shortly before the foot touches the ground. Vertical acceleration in excess of $\ddot{y}_{strike}$ at impact causes transition to Early Stance.
5. Early Stance: The biological knee flexes while the ankle dorsiflexes, resulting in a shortening effective leg length. With the clutch engaged, the exoskeletal knee does not flex and the bow spring bears load, storing energy. The hip flexes, propelling the body forward. The resulting negative rotation of the gyroscope in excess of $\dot{\psi}_{stance}$ causes deactivation of the solenoid and transition to Terminal Stance.
6. Terminal Stance: The center of mass reaches its lowest point, after which the biological knee and ankle reverse direction, resulting in a lengthening effective leg length. Although the solenoid is off, the clutch is bound by the large applied torque. As toe off nears, the effective leg length approaches and eventually exceeds that when the clutch was engaged, allowing it to relax to its disengaged state. The detection of this disengagement by the Break beam sensor causes transition to Preswing.

The solenoid is activated, using a pulse and hold strategy to reduce power consumption, while in the Terminal Swing and Early Stance states. Were the clutch able to engage infinitely quickly, the Swing 2 state could simply monitor for a minimum in the knee encoder and engage the clutch immediately as it transitions to Terminal Swing. In practice, it is necessary to activate the solenoid slightly prior to the true encoder minimum. This prediction is carried out by the latency compensation algorithm.

Latency Compensation

A significant latency is associated with the electromechanical system comprising the solenoid, return spring, and translating clutch plate. Experimentally, the delay from application of 24V to the solenoid to full engagement of the clutch is approximately 30 ms. As this time is comparable to the duration of late swing, it is necessary to compensate for the electromechanical latency, firing the solenoid early to ensure that the clutch is fully engaged at the time of maximum knee extension. The latency compensation algorithm in use during the Swing 2 phase accomplishes this.

One can consider only late swing phase between peak knee flexion and heel strike (isolated by the technique presented above). During this phase, knee angle is approximately parabolic so one may fit the observed encoder counts to a second order polynomial with peak knee extension at the vertex. Using such a continuously generated fit, one can elect to fire the solenoid once the predicted vertex position is less than 30 ms in the future.

Unfortunately, the entirety of late swing is not parabolic; an inflection point exists which varies substantially between wearers and is in general difficult to predict or identify. As the region before this inflection point would skew the regression, it is advantageous to choose to fit to a running window rather than to all data in late swing.

While a closed form to a quadratic least squares regression exists (and in fact can be computable only from running sums), there is a simpler, even less computationally expensive solution. Rather than fitting encoder readings to a quadratic and seeking the vertex, one can fit differentials of encoder readings to a line and seek the zero crossing.

Let $\theta_i$ represent the exoskeletal knee angle i samples prior, so that $\theta_0$ is the current angle and let $\delta\theta_i = \theta_i - \theta_{i+1}$ represent a differential angle between adjacent samples. A sliding window of the most recent W samples may be fit to a line of the form $$\hat{\delta\theta_i} = \frac{ai+b}{d} \quad (4.1)$$

with coefficients given by $$a = -S_0 T_1 - S_1 T_0 \quad (4.2)$$

$$b = S_2 T_0 + S_1 T_1 \quad (4.3)$$

$$d = S_0 S_2 - S_1^2 \quad (4.4)$$

where $$S_k = \sum_{i=0}^{W-1} i^k \quad (4.5)$$

$$T_k = \sum_{i=0}^{W-1} i^k \delta_i \quad (4.6)$$

$$\quad (4.7)$$

so that $$S_0 = \sum_{i=0}^{W-1} 1 = W \quad (4.8)$$

$$S_1 = \sum_{i=0}^{W-1} i = \frac{S_0(S_0-1)}{2} \quad (4.9)$$

-continued $$S_2 = \sum_{i=0}^{W-1} i^2 = \frac{S_1(2S_0-1)}{3} \quad (4.10)$$

$$T_0 = \sum_{i=0}^{W-1} \delta\theta_i = \theta_i - \theta_W \quad (4.11)$$

$$T_1 = \sum_{i=0}^{W-1} i\delta\theta_i = \left(\sum_{i=1}^{W-1} \theta_i\right) - (W-1)\theta_W \quad (4.12)$$

This fit crosses zero, corresponding to the desired knee extremum, in a number of samples given by $$\Delta n_{eta} = -\left(\frac{b}{a}\right) \quad (4.13)$$

or equivalently $$\Delta t_{eta} = -\left(\frac{1}{f}\right)\left(\frac{b}{a}\right) \quad (4.14)$$

where f is the sampling frequency.

Figure 22:
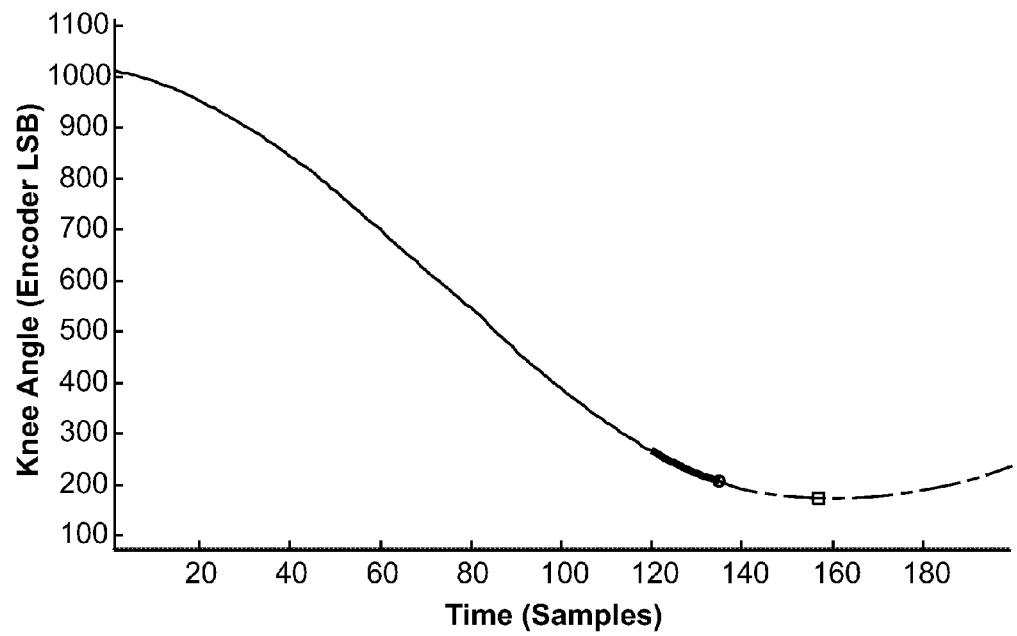
FIG. 22 is a simulation of solenoid latency compensation predicting peak knee extension. Actual exoskeletal knee data recorded at 800 samples per second is used. The bold region represents the window of data used in the final iteration before firing the solenoid. The firing time is denoted by a circle while the predicted extremum is denoted by a square. Data from time after the solenoid firing is dashed. Note the correspondence between the predicted and actual times of peak knee extension.

So, $S_1$, and $S_2$ are computable offline and d need not be computed at all. $T_0$ is trivially calculable and $T_1$ reduces to a running sum and requires incremental corrections only for end points of the sliding window. Thus, this approach is extremely inexpensive computationally. FIGS. 22 and 23 demonstrate its efficacy with a window 16 samples wide and a look ahead threshold of 30 samples.

Pulse-and-Hold Solenoid Activation

In order to minimize clutch engagement time, the solenoid may be driven at $D_{open}$=100% duty cycle, but it is desirable to reduce this voltage once the clutch is fully engaged in order to reduce power consumption and maximize battery life. To this end, a pulse-and-hold strategy is used, settling to an experimentally determined $D_{closed}$=24% duty cycle sufficient to overcome the return spring once the break beam sensor reports full engagement.

Clinical Testing and Results

In order to determine the effect of parallel elasticity at the knee joint on running, an experiment was undertaken in which subjects ran on a treadmill with and without the exoskeleton while instrumented for joint kinematics and kinetics, electromyography, and metabolic demand.

Experimental Design

The proposed exoskeleton provides an elastic element in parallel with the knee during stance phase, but unfortunately a practical device, like that outlined above with reference to FIGS. 1-13, also influences the body in several other ways due to its mass and means of attachment. Additional mass of the exoskeleton has a gravitational effect as hip extensors and knee flexors must lift the mass during early swing and an inertial effect as hip flexors must accelerate the mass during swing. Finally, attachment to the body, as discussed above with reference to FIGS. 14A-17C, is difficult to accomplish without some constriction, which limits range of motion and causes discomfort. In order to isolate the effect of elasticity, experiments were conducted in three conditions—control, in which subjects ran in self selected footwear with no experimental apparatus other than those required for instrumentation, inactive, in which subjects wore the investigational knee brace with the power off, contributing zero stiffness but offering the same secondary affects associated with mass and restricted movement, and active, in which subjects wore the investigational knee brace with the power on, contributing a non-zero parallel stiffness during stance phase.

TABLE 5

Descriptive measurements of the six recruited subjects and the number of steps analyzed for each in the three trials. Fewer steps than expected were available for S1 due to lost markers, for S5 due to an equipment failure, and for S6 due to early exhaustion.

|  | Age yr | Height cm | Leg Length cm | Mass kg | Cadence Steps/s | Control Steps | Inactive Steps | Active Steps |
|---|---|---|---|---|---|---|---|---|
| S1 | 27 | 175 | 96 | 57 | 172 | 30 | 30 | 11 |
| S2 | 19 | 196 | 107 | 61 | 152 | 50 | 50 | 50 |
| S3 | 44 | 180 | 99 | 74 | 175 | 50 | 50 | 50 |
| S4 | 25 | 185 | 102 | 82 | 162 | 50 | 50 | 50 |
| S5 | 20 | 180 | 85 | 77 | 162 | 50 | 50 | 28 |
| S6 | 34 | 170 | 93 | 66 | 166 | 50 | 33 | 37 |

Six male subjects (Mass 69±8 kg, Height 181±8 cm), described in Table 5, were recruited from a pool of healthy recreational runners having leg length (>90 cm) and circumference (45-55 cm at the thigh, 20-30 cm at the shin) consistent with the investigational knee brace.

Each subject ran with the device active for a training session of at least thirty minutes on a day prior to instrumented trials. Subjects trained initially on open ground then continued on a treadmill wearing a fall prevention harness (Bioness, Valencia, Calif., USA). During this training session, subjects with a gait insufficiently wide to prevent collision between the braces or with stance knee extension insufficient to ensure disengagement of the clutch were disqualified on the basis of safety. During the experimental session, a nominal 0.9 Nm/° elastic element was used. This relatively small stiffness proved necessary due to the effects of series compliance in the harness and the tendency of the biological knee to resist a stiffer exoskeleton by shifting anteriorly in the brace.

At the start of the experimental session, each subject's self-selected step frequency was measured while running on the treadmill at 3.5 m/s without the investigational knee brace. The time necessary to complete 30 strides was measured by stopwatch after approximately one minute of running. This cadence (166±9 steps/s) was enforced by metronome for all subsequent trials.

After being instrumented for electromyography and motion capture, subjects then ran on the instrumented treadmill at 3.5 m/s in the control, inactive, and active conditions. Trial order was randomized, excepting that inactive and active conditions were required to be adjacent, so as to require only a single fitting of the investigational device in each session. Each running trial was seven minutes in length, with an intervening rest period of at least as long. Resting metabolism was also measured for five minutes at both the start and end of the experimental session. Sessions lasted approximately three hours, including 21 minutes of treadmill running Instrumentation and Processing During the experimental session, each subject was instrumented for joint kinematics and kinetics, electromyography, and metabolic demand.

Subject motion was recorded using an 8 camera passive marker motion capture system (VICON, Oxford, UK). Adhesive-backed reflective markers were affixed to subjects using a modified Cleveland Clinic marker set for the pelvis and right leg (Left and right ASIS and Trochanter, three marker pelvis cluster, four marker thigh cluster, medial and lateral epicondyle, four marker shin cluster, medial and lateral malleolus, calcaneus, foot, fifth metatarsal). For inactive and active trials, the termination points of the exoskeletal spring were also marked. Motion data was recorded at 120 Hz and low filtered using a $2^{nd}$ order Butterworth filter with a 10 Hz cutoff. Ground reaction forces were recorded at 960 Hz using a dual belt instrumented treadmill (BERTEC, Columbus, Ohio, USA) and low pass filtered using a 2nd order Butterworth filter with a 35 Hz cutoff. Following calibration using a static standing trial, Visual3D (C-Motion Inc, Germantown, Md., USA) modeling software was used to reconstruct joint kinematics and kinetics and center of mass trajectories, with right-left leg symmetry assumed.

Fifty steps from each trial were analyzed to determine average leg and joint stiffness. Due to technical difficulties associated with loss or migration of motion capture markers and the appearance of false markers due to reflectivity of the exoskeleton, some motion capture recordings proved unusable. Consequently, the exact timing of the steps used varies between subjects and it was not possible to analyze fifty steps for all trials, as indicated in Table 5. In general, the earliest available reconstructions a minimum of one minute into the trial were used, to minimize effects of fatigue.

$k_{leg}$ and $k_{vert}$ were calculated for each step using Equation 1.2 and Equation 1.1 with center of mass displacements determined by Visual3D through integration of reaction forces as in G. A. Cavagna, Force Plates as Ergometers, Journal of Applied Philosophy, 39(1):174-179, 1975. This effective spring is characterized by $k_{vert}$, given by $$k_{vert} = \frac{F_{z,peak}}{\Delta y} \quad (1.1)$$

where $F_{z,peak}$ is the maximum vertical component of the ground reaction force and $\Delta y$ is the vertical displacement of the center of mass.

Due to the angle subtended, however, the effective leg spring, characterized by $k_{leg}$, is compressed from its rest length $L_o$ by $\Delta L$ much larger than $\Delta y$, so that $$k_{leg} = \frac{F_{z,peak}}{\Delta L} \quad (1.2)$$

Unlike the effective leg spring, the knee and ankle experience different stiffnesses in absorptive (early) stance and generative (late) stance. Consequently, stiffnesses of these joints were estimated individually for the two phases using $$\kappa_{joint,abs} = \frac{M_{joint,peak} - M_{joint,HS}}{\theta_{point,peak} - \theta_{joint,HS}} \quad (5.1)$$

$$\kappa_{joint,gen} = \frac{M_{joint,peak} - M_{joint,TO}}{\theta_{point,peak} - \theta_{joint,TO}} \quad (5.2)$$

where peak represents the instant of peak torque in the joint and HS and TO represent heel-strike and toe-off respectively.

Muscle activation was gauged noninvasively using surface electromyography (EMG), which responds to the membrane potential of a muscle beneath skin. Electrodes were placed above the right soleus, lateral gastrocnemius, tibialis anterior, vastus lateralis, rectus femoris, biceps femoris, gluteus maximus, and illiopsoas. Wires were taped to skin and routed an amplifier (Biometrics Ltd, Ladysmith, Va., USA) clipped to the chest harness containing the cardiopulmonary test system. An EMG system with low profile electrodes was used to facilitate placement around the harness. Nonetheless, placement of the electrode on the lateral gastrocnemius was suboptimal due to the positioning of harness straps. A reference electrode was at tached to the wrist. Prior to the first running trial, recordings were made of maximal voluntary contractions (MVCs) in each muscle.

Electromyography was recorded at 960 Hz then filtered into a low bandwidth signal indicative of activation by the following filter chain (Robert Merletti, "Standards for Reporting EMG Data," Technical Report, Politecnico di Tornino, 1999) (Clancy et al, "Sampling, Noise-Reduction, and Amplitude Estimation Issues in Surface Electromyography," Journal of Electromyography and Kinesiology, 12:1-16, 2002.) DC block, 60 Hz notch filter to eliminate mains hum, a 50 ms moving average filter to eliminate motion artifacts, and rectification with a 200 ms moving average filter to recover the envelope. Finally, activation for each muscle was normalized to the maximum activation seen in stride averaged control trials for that subject.

Figure 24:
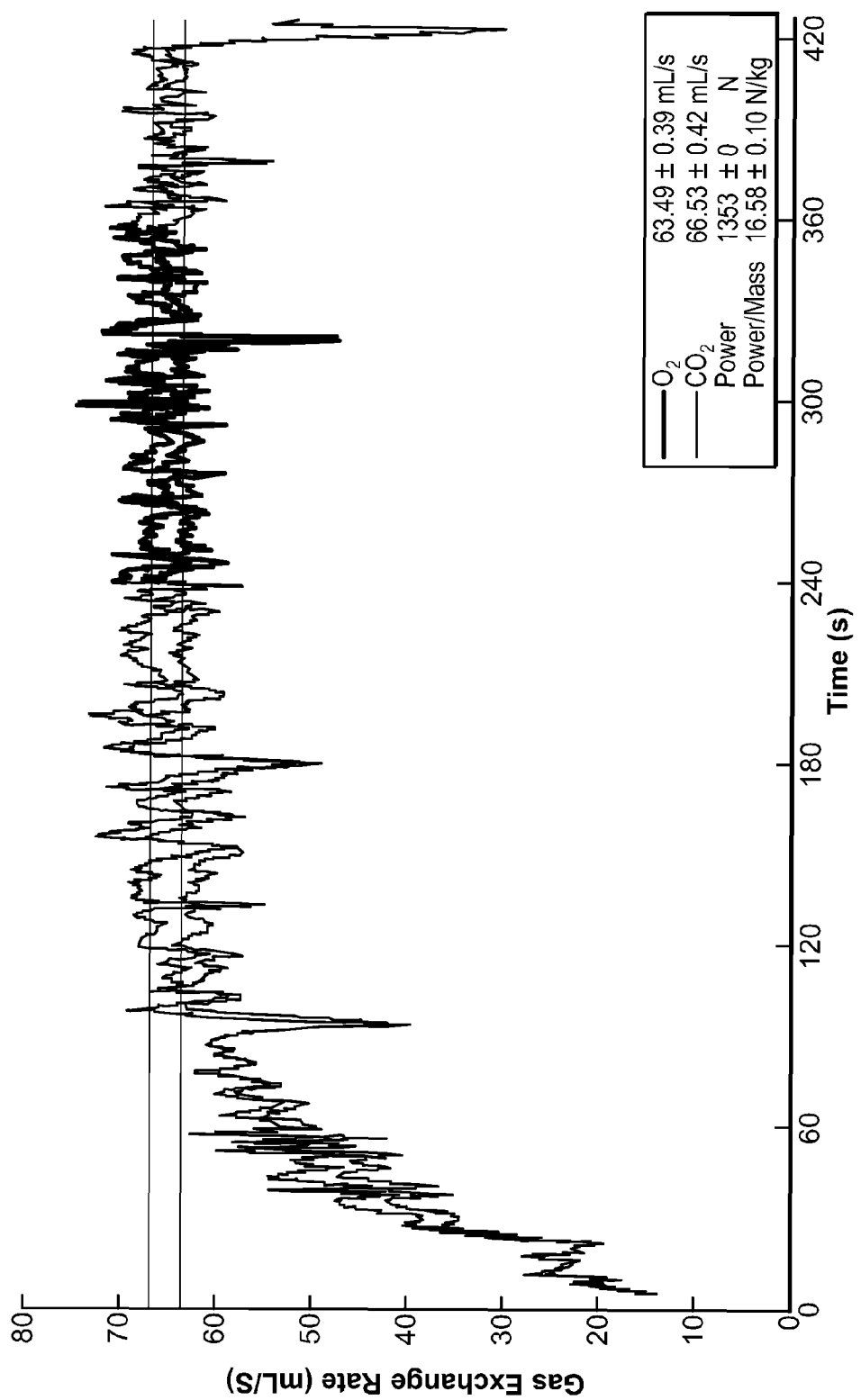
FIG. 24 is a plot of metabolic demand calculation.

Metabolic demand was measured noninvasively using a mobile cardiopulmonary exercise test system (VIASYS Healthcare, Yorba Linda, Calif., USA), which measures rates of oxygen consumption and carbon dioxide production through a face mask. Once sub-maximal steady state metabolism was achieved, total metabolic power was deduced from linear expressions of the form $$P = K_{O_2} V_{O_2}' + K_{CO_2} V_{CO_2}' \quad (5.3)$$

where $V'_{O2}$ and $V'C_{O2}$ represent average rates of oxygen inhalation and carbon dioxide exhalation and $K_{O2}$ and $K_{co2}$ are constants which have been well documented. Brockway's (J. M. Brockway, "Derivation of Formulae Used to Calculate Energy Expenditure in Man," Human Nutrition Clinical Nutrition, 41: 463-471, 1987.) For values $K_O$=16.58 kW/L and $K_{CO2}$=4.5 kW/L were used. Average rates were calculated over a two minute window during steady state metabolism from 4:00 to 6:00 within each seven minute trial, as shown in FIG. 24. In addition to the running conditions, resting metabolic power was also measured with the subject standing for five minutes.

Such measures of metabolic power are only valid if the contributions of anaerobic metabolism are small. This was assured by monitoring the ratio of volume of carbon dioxide exhaled to oxygen inhaled, known as the respiratory exchange ratio. Oxidative metabolism was presumed to dominate while this ratio was below 1.1.

More details of the instrumentation used here can be found in (Farris et al., "The Mechanics and Energetics of Human Walking and Running, a Joint Level Perspective," Journal of the Royal Society Interface, 9(66):110-118, 2011), in which identical instrumentation and signal processing were used, with the omission of electromyography.

Results

Joint and leg stiffnesses calculated for each of the six subjects as described above are presented in Table 6 and Table 7, with averaged stiffnesses presented in Table 9. Subjects S1, S2, S3, and S4 exhibited similar gross kinematics in all three conditions. S5 exhibited similar kinematics in the inactive condition, but transitioned to a toe-striking gait, with significant ankle plantar flexion at strike in the active condition. Consequently, S5's active mechanics are not considered in population averages. S6's mechanics are similarly omitted, as he was visibly fatigued and failed to complete either the active or inactive trials.

Metabolic demand, calculated using Equation 5.3 is presented in Table 8 for resting, control, inactive, and active conditions, with averaged demand presented in Table 9.

TABLE 7

| | Control | | Inactive | | Active | |
|---|---|---|---|---|---|---|
| | $k_{leg}$ N/kg m/m | $k_{vert}$ N/kg m/m | $k_{leg}$ N/kg m/m | $k_{vert}$ N/kg m/m | $k_{leg}$ N/kg m/m | $k_{vert}$ N/kg m/m |
| S1 | 196 ± 14 | 692 ± 122 | 204 ± 16 | 820 ± 165↑ | 218 ± 26 | 793 ± 182 |
| S2 | 191 ± 16 | 608 ± 104 | 198 ± 15 | 688 ± 138↑ | 204 ± 9 | 708 ± 115 |
| S3 | 241 ± 15 | 733 ± 100 | 249 ± 16↑ | 815 ± 135↑ | 280 ± 23↑ | 956 ± 210↑ |
| S4 | 153 ± 8 | 499 ± 57 | 165 ± 11↑ | 592 ± 125↑ | 155 ± 7↓ | 530 ± 52↓ |
| S5 | 166 ± 16 | 626 ± 130 | 169 ± 15 | 716 ± 260 | 205 ± 16↑ | 694 ± 200 |
| S6 | 182 ± 11 | 727 ± 115 | 185 ± 10 | 664 ± 105 | 193 ± 15 | 734 ± 109↑ |

Effective leg stiffnesses, normalized by subject mass and leg length, calculated for the six subjects. Uncertainties reflect the standard deviation associated with step-to-step variation. Arrows indicate the direction of statistically significant significant differences at the 1% level within a given subject from the control to inactive condition or from the inactive to active condition. Significance was computed using a two sided t-test. Because the uncertainties reported here do not reflect trial-to-trial variation and due to the large number of comparisons (60) made within this table, these marks should be taken as suggestive of greater trends and not treated as meaningful in isolation.

TABLE 6

| | Control | | Inactive | | Active | | Control | |
|---|---|---|---|---|---|---|---|---|
| | $K_{ankle,Abs}$ Nm/kg * | $K_{ankle,Gen}$ Nm/kg * | $K_{ankle,Abs}$ Nm/kg * | $K_{ankle,Gen}$ Nm/kg * | $K_{ankle,Abs}$ Nm/kg * | $K_{ankle,Gen}$ Nm/kg * | $K_{knee,Abs}$ Nm/kg * | $K_{knee,Gen}$ Nm/kg * |
| S1 | 0.136 ± 0.012 | 0.078 ± 0.003 | 0.134 ± 0.012 | 0.087 ± 0.003↑ | 0.183 ± 0.022↑ | 0.094 ± 0.012 | 0.120 ± 0.022 | 0.081 ± 0.007 |
| S2 | 0.182 ± 0.012 | 0.079 ± 0.006 | 0.165 ± 0.012↓ | 0.083 ± 0.005↑ | 0.174 ± 0.016↑ | 0.085 ± 0.007 | 0.113 ± 0.022 | 0.106 ± 0.010 |
| S3 | 0.181 ± 0.013 | 0.077 ± 0.003 | 0.165 ± 0.010↓ | 0.079 ± 0.003↑ | 0.174 ± 0.013↑ | 0.086 ± 0.005↑ | 0.132 ± 0.021 | 0.140 ± 0.018 |
| S4 | 0.176 ± 0.014 | 0.065 ± 0.003 | 0.148 ± 0.012↓ | 0.069 ± 0.002↑ | 0.160 ± 0.011↑ | 0.068 ± 0.003 | 0.088 ± 0.011 | 0.091 ± 0.007 |
| S5 | 0.153 ± 0.009 | 0.075 ± 0.004 | 0.138 ± 0.006↓ | 0.081 ± 0.005↑ | 0.142 ± 0.017 | 0.096 ± 0.004↑ | 0.093 ± 0.016 | 0.077 ± 0.009 |
| S6 | 0.110 ± 0.017 | 0.059 ± 0.007 | 0.185 ± 0.015↑ | 0.085 ± 0.002↑ | 0.123 ± 0.011↓ | 0.078 ± 0.004↓ | 0.099 ± 0.021 | 0.066 ± 0.007 |

| | Inactive | | Active | | | | | |
|---|---|---|---|---|---|---|---|---|
| | $K_{knee,Abs}$ Nm/kg * | $K_{knee,Gen}$ Nm/kg * | $K_{knee,Abs}$ Nm/kg * | $K_{knee,Gen}$ Nm/kg * | $K_{exo,Abs}$ Nm/kg * | $K_{exo,Gen}$ Nm/kg * | $K_{blocking,Abs}$ Nm/kg * | $K_{blocking,Gen}$ Nm/kg * |
| S1 | 0.105 ± 0.016↓ | 0.066 ± 0.009↓ | 0.124 ± 0.023 | 0.085 ± 0.013↑ | 0.019 ± 0.005 | 0.014 ± 0.005 | 0.108 ± 0.021 | 0.072 ± 0.013 |
| S2 | 0.111 ± 0.019 | 0.087 ± 0.011↓ | 0.113 ± 0.016 | 0.089 ± 0.011 | 0.025 ± 0.006 | 0.020 ± 0.003 | 0.089 ± 0.015↓ | 0.069 ± 0.011↓ |
| S3 | 0.106 ± 0.017↓ | 0.092 ± 0.005↓ | 0.130 ± 0.024↑ | 0.107 ± 0.010↑ | 0.017 ± 0.002 | 0.016 ± 0.002 | 0.114 ± 0.024 | 0.091 ± 0.009 |
| S4 | 0.114 ± 0.016↑ | 0.089 ± 0.007 | 0.110 ± 0.015 | 0.088 ± 0.006 | 0.011 ± 0.001 | 0.010 ± 0.002 | 0.100 ± 0.015↓ | 0.078 ± 0.006↓ |
| S5 | 0.088 ± 0.012 | 0.061 ± 0.006↓ | 0.062 ± 0.014↓ | 0.056 ± 0.007↓ | 0.015 ± 0.062 | 0.041 ± 0.053 | 0.060 ± 0.070 | 0.041 ± 0.019↓ |
| S6 | 0.145 ± 0.018↑ | 0.103 ± 0.010↑ | 0.093 ± 0.030↓ | 0.073 ± 0.008↓ | 0.020 ± 0.027 | 0.020 ± 0.014 | 0.070 ± 0.030↓ | 0.056 ± 0.009↓ |

(a) Ankle stiffness, measured in absorptive and generative stance, normalized by body mass (b) Knee stiffness, measured in absorptive and generative stance, normalized by body mass Effective joint stiffnesses, normalized by subject mass, calculated for the six subjects. Uncertainties reflect the standard deviation associated with step-to-step variation. Because the control and inactive condition impose zero exoskeletal stiffness and therefore result in equal total and biological knee stiffnesses, exoskeletal and biological contributions at the knee are listed only for the active condition. Arrows indicate the direction of statistically significant differences at the 1% level within a given subject from the control to inactive condition or from the inactive to active condition. Significance was computed using a two sided t-test. Because the uncertainties reported here do not reflect trial-to-trial variation and due to the large number of comparisons (60) made within this table, these marks should be taken as suggestive of greater trends and not treated as meaningful in isolation.

TABLE 8

Metabolic demands, normalized by subject mass, calculated for the six subjects. Uncertainties reflect the standard error associated with breath-to-breath variation. Arrows indicate the direction of statistically significant differences at the 1% level within a given subject from the control to inactive condition or from the inactive to active condition. Significance was computed using a two sided z-test. Because the uncertainties reported here do not reflect trial-to-trial variation, these marks should be taken as suggestive of greater trends and not treated as meaningful in isolation.

|    | Resting W/kg | Control W/kg | Inactive W/kg | Active W/kg |
|----|----|----|----|----|
| S1 | 1.7 ± 0.2 | 15.7 ± 0.1 | 21.2 ± 0.1↑ | 20.7 ± 0.1↓ |
| S2 | 1.3 ± 0.2 | 17.2 ± 0.2 | 19.0 ± 0.3↑ | 19.7 ± 0.3 |
| S3 | 1.1 ± 0.1 | 16.6 ± 0.1 | 20.6 ± 0.0↑ | 20.3 ± 0.1↓ |
| S4 | 1.4 ± 0.1 | 16.6 ± 0.1 | 19.6 ± 0.1↑ | 20.4 ± 0.1↑ |
| S5 | 1.2 ± 0.1 | 17.2 ± 0.3 | 16.9 ± 0.1 | — |
| S6 | 1.7 ± 0.1 | 16.2 ± 0.2 | — | — |

TABLE 9

|   |   | Control | Inactive | Active |
|---|---|---|---|---|
| $k_{ankle,Abs}$ | $\left(\frac{Nm/kg}{\circ}\right)$ | 0.169 ± 0.022 | 0.153 ± 0.015 | 0.173 ± 0.010 |
| $k_{ankle,Gen}$ | $\left(\frac{Nm/kg}{\circ}\right)$ | 0.075 ± 0.006 | 0.079 ± 0.008↑ | 0.083 ± 0.011 |
| $k_{knee,Abs}$ | $\left(\frac{Nm/kg}{\circ}\right)$ | 0.113 ± 0.019 | 0.109 ± 0.004 | 0.119 ± 0.009 |
| $k_{knee,Gen}$ | $\left(\frac{Nm/kg}{\circ}\right)$ | 0.105 ± 0.026 | 0.084 ± 0.012 | 0.092 ± 0.010 |
| $k_{exo,Abs}$ | $\left(\frac{Nm/kg}{\circ}\right)$ | — | — | 0.018 ± 0.006 |
| $k_{exo,Gen}$ | $\left(\frac{Nm/kg}{\circ}\right)$ | — | — | 0.015 ± 0.004 |
| $k_{bioknee,Abs}$ | $\left(\frac{Nm/kg}{\circ}\right)$ | 0.113 ± 0.019 | 0.109 ± 0.004 | 0.102 ± 0.011 |
| $k_{bioknee,Gen}$ | $\left(\frac{Nm/kg}{\circ}\right)$ | 0.105 ± 0.026 | 0.084 ± 0.012 | 0.078 ± 0.010 |
| $k_{leg}$ | $\left(\frac{N/kg}{m/m}\right)$ | 195 ± 36 | 204 ± 35 | 214 ± 52 |
| $k_{vert}$ | $\left(\frac{N/kg}{m/m}\right)$ | 633 ± 103 | 729 ± 110↑ | 747 ± 178 |
| $P_{met}$ | $\left(\frac{W}{kg}\right)$ | 16.5 ± 0.7 | 20.3 ± 0.8 | 20.3 ± 0.4 |

Mean joint stiffnesses, leg stiffnesses, and metabolic demands. Uncertainties reflect the standard deviation associated with subject-to-subject variation. Arrows indicate the direction of statistically significant differences at the 5% level from the control to inactive condition or from the inactive to active condition. Significance was determined using a post-hoc paired two-Šidák-corrected test, following a repeated measures ANOVA. Due to atypical kinematics, results for S5 and S6 are omitted, though S5's data are used to compare control and inactive conditions; see text for details.

Average Mechanics and Metabolic Demand

For each stiffness as well as metabolic demand, a repeated measures ANOVA was conducted to determine significance of trends apparent above. Due to the outlying nature of S6's inactive trial and S5's active trial, their data for all conditions was omitted from this test. For each stiffness found to vary among the three groups, a post-hoc two-sided paired t-test was conducted using Sidak correction to compare the control and inactive conditions and inactive and active conditions, so that P=0.0253 is considered significant.

ANOVA suggests total leg stiffness varies among the conditions (P=0.08), with post-hoc paired t-testing revealing that the observed increase in k leg due to inactive mass is significant (P<0.01), but that no significant difference exists between the inactive and active conditions. This suggestion that increased mass at the knee increases leg stiffness is interesting, particularly in light of He et al., "Mechanics of Running Under Simulated Low Gravity," Journal of Applied Physiology, 71:863-870, 1991 finding that leg stiffness does not vary when gravity is reduced. Moreover, if leg stiffness is normalized by total mass rather than by subject mass (as was not necessary in He et al., "Mechanics of Running Under Simulated Low Gravity, Journal of Applied Physiology, 71:863-870, 1991), no evidence of increase is found.

ANOVA suggests variation in total generative phase knee stiffness (P=0.10) and finds significant variation in biological generative phase knee stiffness (P=0.04). Post-hoc testing suggests that generative phase knee stiffness decreases due to the additional mass (P=0.10), but does not find evidence of difference between the inactive and active conditions.

Additionally, a significant variation in ankle stiffness in generation (P=0.02), with post-hoc testing suggesting a difference between the control and inactive conditions (P=0.06) but not between inactive and active conditions.

A suggestive difference exists in metabolic demand between the control and inactive conditions for all subjects for whom metabolic data was available in these conditions (P=0.04, not quite significant at the 5% level with the Sidak correction). This is misleading, however, as the respiratory exchange ratio is notably higher for trials in the inactive and active condition than for trials in the control condition. Though always below 1.1, this shift in respiratory exchange ratio implies that some anaerobic contribution is present when the brace is worn, making comparisons between the control and inactive case tenuous. It is worth noting that if S5's anomalously low demand in the inactive condition is omitted as an outlier, the difference between these conditions becomes significant, as is expected from subjective reactions to running with the additional mass.

There is no evidence against the null hypotheses that leg stiffness and knee stiffness are each unchanged by the presence of an external parallel spring at the knee.

Subject Variation in Response to Intervention

Figure 25:
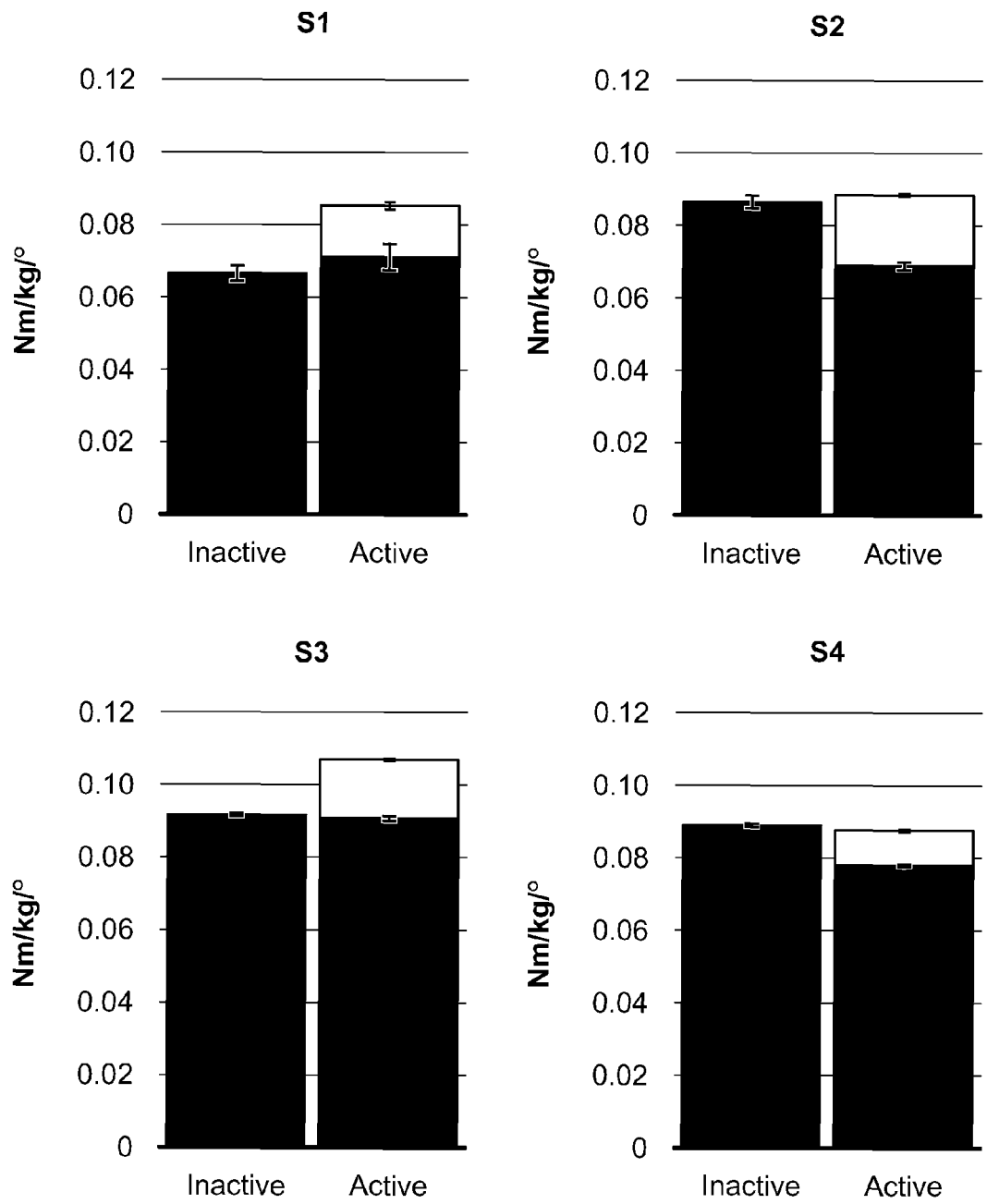
FIG. 25 is a depiction of biological (dark) and exoskeletal (light) generative phase knee stiffness for several subjects in the inactive and active conditions.

Closer examination of Table 6 suggests that the population may be divided into two groups according to level of training. As shown in FIG. 25, trained competitive marathoners S1 and S3 appear to exhibit increased total knee stiffness in the active condition, while recreational runners S2 and S4 exhibit unchanged knee stiffness despite the external stiffness. While statistics for such a small sample must be approached cautiously, a two sided paired t-test suggests increased total knee stiffness in both absorption and generation in marathoners (P=0.07 in both cases) with no corresponding effect in recreational runners (P=0.80 in both cases). Ankle stiffness in generation is also found to increase in the active case in marathoners (P<0.01) but not in recreational runners (P=0.50). Marathoners S1 and S3 also exhibit small (2%) reductions in metabolic demand above resting while S2 and S4 do not, though this effect is not statistically significant. Verifying these apparent differences in stiffness and metabolic demand based on runner training would require subsequent investigation with larger samples of recreational and trained runners, however.

EQUIVALENTS

While this invention has been particularly shown and described with reference to various embodiments thereof, it will be understood by those skilled in the art that various changes in form and details may be made therein without departing from the scope of the invention encompassed by the appended claims.

The relevant teachings of all references cited are incorporated by reference herein in their entirety.

What is claimed is:

1. A clutched elastic element exoskeleton, comprising:
   a) a longitudinal harness, including
      i) a proximal component, and
      ii) a distal component;
   b) at least one elastic element linking the proximal and distal components; and
   c) a rotary clutch assembly linked in series to one end of each elastic element, wherein the rotary clutch assembly and the elastic element span the proximal and distal components, and wherein the elastic element is rotatable about a center of rotation at the rotary clutch.

2. The exoskeleton of claim 1, wherein the elastic element is selected from at least one member of the group consisting of a leaf spring, a compression spring and a tension spring.

3. The exoskeleton of claim 2, wherein the elastic element includes at least one leaf spring.

4. The exoskeleton of claim 3, wherein the elastic element includes at least two leaf springs.

5. The exoskeleton of claim 4, wherein at least one of the leaf springs is linked to the proximal component, at least another of the leaf springs is linked to the distal component, and the rotary clutch assembly links the proximal and distal leaf springs in series.

6. The exoskeleton of claim 5, wherein the proximal leaf spring is linked to the proximal component at a proximal hinge that is proximal to the rotary clutch assembly, whereby the proximal leaf spring can rotate at the hinge about an axis that is substantially parallel to an axis of rotation of the rotary clutch assembly.

7. The exoskeleton of claim 6, wherein the distal leaf spring is linked to the distal component at a distal hinge that is distal to the rotary clutch assembly, whereby the distal leaf spring can rotate at the hinge about an axis that is substantially parallel to an axis of rotation of the rotary clutch assembly.

8. The exoskeleton of claim 5, wherein the rotary clutch assembly includes an interference clutch.

9. The exoskeleton of claim 8, wherein the rotary clutch assembly includes a gear box.

10. The exoskeleton of claim 9, wherein the interference clutch includes mating castle teeth.

11. The exoskeleton of claim 9, wherein the interference clutch includes mating saw teeth.

12. The exoskeleton of claim 11, wherein the angled saw teeth are asymmetrical.

13. The exoskeleton of claim 12, wherein the gear box further includes a planetary gear.

14. The exoskeleton of claim 13, wherein the actuator is a solenoid.

15. The exoskeleton of claim 14, wherein the rotary clutch assembly includes a distal mount and the planetary gear includes a ring gear, wherein the ring gear is fixedly connected to the distal mount and the distal mount is fixedly connected to one end of the distal leaf spring.

16. The exoskeleton of claim 15, wherein the planetary gear further includes a sun gear, and a plurality of planet gears linking the ring gear to the sun gear.

17. The exoskeleton of claim 16, wherein the interference clutch includes a rotary clutch plate and a translating clutch plate, the rotary clutch plate being fixedly linked to the sun gear and the translating clutch plate being mated to the rotary clutch plate at the saw teeth.

18. The exoskeleton of claim 17, wherein the translating clutch plate is fixedly linked to the solenoid, whereby the translating clutch plate and the rotary clutch plate engage by actuation of the solenoid, thereby engaging the rotary clutch assembly.

19. The exoskeleton of claim 18, wherein the rotary clutch assembly includes a proximal mount fixedly connected to one end of the proximal leaf spring, wherein the solenoid is fixedly linked to the translating clutch plate and rotationally fixed to the proximal mount.

20. The exoskeleton of claim 19, further including a spring that biases the translating plate away from the rotary clutch plate, thereby causing the translating clutch plate to disengage from the rotary clutch plate when the solenoid is not actuated.

21. The exoskeleton of claim 20, further including an optical encoder on at least one planet gear to detect the rate of rotation of the planet gear.

22. The exoskeleton of claim 21, wherein the ratio of rotation of the ring gear to the sun gear is less than 1:1.

23. The exoskeleton of claim 21, wherein the ratio of rotation of the ring gear to the sun gear is about 1:2.2.

24. The exoskeleton of claim 23, wherein the rotary clutch assembly is self-contained.

25. The exoskeleton of claim 24, wherein the rotary clutch assembly further includes at least one of:
   a) an inertial measurement unit;
   b) a solenoid driver;
   c) a reflective optical encoder;
   d) an optical break-beam;
   e) a microcontroller;
   f) an LED driver;
   g) a USB interface;
   h) a micro SD card;
   i) a real-time clock;
   j) a switching power supply; and
   k) a battery protection unit.

26. The exoskeleton of claim 1, wherein a major longitudinal axis of the elastic element extends through and is rotatable about the center of rotation at the rotary clutch.

27. A clutched elastic element exoskeleton, comprising:
   a) a longitudinal harness, including
      i) a proximal component, and
      ii) a distal component;
   b) an elastic element and clutch assembly, including
      i) a proximal elastic element,
      ii) a distal elastic element, and
      iii) a rotary clutch linked in series to one end of each elastic element, wherein the rotary clutch and the elastic elements span the proximal and distal components, and wherein the elastic elements are rotatable about a center of rotation of the clutch.

* * * * *